(12) United States Patent
Ando

(10) Patent No.: US 9,683,943 B2
(45) Date of Patent: *Jun. 20, 2017

(54) INSPECTION APPARATUS, INSPECTION METHOD, AND PROGRAM

(71) Applicant: Keyence Corporation, Osaka (JP)

(72) Inventor: Daisuke Ando, Osaka (JP)

(73) Assignee: Keyence Corporation, Osaka (JP)

(*) Notice: Subject to any disclaimer, the term of this patent is extended or adjusted under 35 U.S.C. 154(b) by 71 days.

This patent is subject to a terminal disclaimer.

(21) Appl. No.: 14/718,110

(22) Filed: May 21, 2015

(65) Prior Publication Data

US 2015/0355103 A1    Dec. 10, 2015

(30) Foreign Application Priority Data

Jun. 9, 2014   (JP) ................................. 2014-119100

(51) Int. Cl.
*G06K 9/00*      (2006.01)
*G01N 21/88*     (2006.01)
*G06T 7/00*      (2017.01)
*G06T 7/586*     (2017.01)

(52) U.S. Cl.
CPC ..... *G01N 21/8806* (2013.01); *G01N 21/8851* (2013.01); *G06T 7/0004* (2013.01); *G06T 7/586* (2017.01); *G01N 21/8803* (2013.01); *G01N 2201/06* (2013.01); *G06T 2207/10152* (2013.01); *G06T 2207/20016* (2013.01); *G06T 2207/30164* (2013.01)

(58) Field of Classification Search
None
See application file for complete search history.

(56) References Cited

U.S. PATENT DOCUMENTS

| | | | |
|---|---|---|---|
| 6,686,921 B1* | 2/2004 | Rushmeier | G06T 7/0073 345/423 |
| 7,019,826 B2* | 3/2006 | Vook | G06T 7/0002 250/559.34 |
| 7,558,370 B2* | 7/2009 | Sommer, Jr. | G01V 5/0016 378/57 |
| 9,234,852 B2* | 1/2016 | Gladnick | G01N 21/8806 |
| 9,404,739 B2* | 8/2016 | Nakatsukasa | G01B 11/25 |
| 2004/0184031 A1* | 9/2004 | Vook | G06T 7/0002 356/237.1 |

(Continued)

FOREIGN PATENT DOCUMENTS

JP    2007-206797    8/2007

*Primary Examiner* — Feng Niu
(74) *Attorney, Agent, or Firm* — Kilyk & Bowersox, P.L.L.C.

(57) ABSTRACT

To facilitate setting of a parameter at the time of generating an inspection image from an image acquired by using a photometric stereo principle. A photometric processing part generates an inspection image based on a plurality of luminance images acquired by a camera. A display control part and a display part switch and display the luminance image and the inspection image, or simultaneously display these images. An inspection tool setting part adjusts a control parameter of the camera and a control parameter of an illumination apparatus. Further, when the control parameter is adjusted, the display control part updates the image being displayed on the display part to an image where the control parameter after the change has been reflected.

18 Claims, 31 Drawing Sheets

(56) References Cited

U.S. PATENT DOCUMENTS

| | | | |
|---|---|---|---|
| 2005/0094891 A1* | 5/2005 | Stavely | H04N 1/4072 382/274 |
| 2009/0225201 A1* | 9/2009 | Abe | G06T 5/009 348/241 |
| 2011/0310270 A1* | 12/2011 | Gladnick | G01N 21/8806 348/229.1 |
| 2015/0355104 A1* | 12/2015 | Matsuda | G01N 21/8806 356/237.2 |
| 2015/0358602 A1* | 12/2015 | Mayumi | G06T 7/0073 348/46 |

* cited by examiner $$\begin{pmatrix} I_1 \\ I_2 \\ I_3 \\ I_4 \end{pmatrix} = \rho L \begin{pmatrix} s_{11} & s_{12} & s_{13} \\ s_{21} & s_{22} & s_{23} \\ s_{31} & s_{32} & s_{33} \\ s_{41} & s_{42} & s_{43} \end{pmatrix} \begin{pmatrix} n_x \\ n_y \\ n_z \end{pmatrix}$$

··· EXPRESSION 1

$$z_{x,y}^{n+1} = \frac{1}{4}\left(z_{x+1,y}^n + z_{x,y+1}^n + z_{x-1,y}^n + z_{x,y-1}^n\right) \\ - \frac{w}{8}\left(p_{x+1,y} - p_{x-1,y} + q_{x,y+1} - q_{x,y-1}\right)$$

··· EXPRESSION 2

INSPECTION APPARATUS, INSPECTION METHOD, AND PROGRAM

CROSS-REFERENCE TO RELATED APPLICATIONS

The present application claims foreign priority based on Japanese Patent Application No. 2014-119100, filed Jun. 9, 2014, the contents of which is incorporated herein by reference.

BACKGROUND OF THE INVENTION

1. Field of the Invention

The present invention relates to an inspection apparatus, an inspection method, and a program.

2. Description of Related Art

In order to measure an accurate three-dimensional shape of a workpiece (inspection target product) by using a photometric stereo principle, there is required an illumination light source whose illumination light is incident on each surface of the workpiece with a uniform light amount. Further, an angle of incidence of the illumination light is required to be known. Moreover, since the angle of incidence of light should not change in accordance with a region of the workpiece, there is required an illumination light source having a size corresponding to the size of the workpiece to be inspected. Furthermore, scale information (actual dimension per pixel) of an image captured by a camera is also required. A visual inspection apparatus is often installed by a user, and it is difficult for the user to satisfy these strict installation conditions. Therefore, according to JP 2007-206797 A, a dedicated apparatus formed by integrating illumination and a camera is proposed, to thereby reduce a burden of installation of the user.

Incidentally, in order to generate an inspection image from a plurality of luminance images with respectively different illumination directions, a variety of control parameters are required to be set. For example, a light amount of the illumination light source, a shutter speed of the camera and the like are required to be appropriately set. The user checks a change in luminance image of the workpiece acquired by the camera while adjusting these control parameters, to search for appropriate control parameters.

However, since an inspection image used for inspection in the inspection apparatus is an image generated from luminance images by computing, even when the luminance images are checked, it is not easy to instinctively see whether or not the inspection image is correct. The inspection image may be displayed to allow the user to check the image, but even when an imaging condition is adjusted, the inspection image may not change in a manner easily seen instinctively. Therefore, even when only the inspection image is displayed, it may be difficult for the user to adjust the control parameter.

SUMMARY OF THE INVENTION

Therefore, an object of the present invention is to facilitate setting of a parameter at the time of generating an inspection image from an image acquired by using a photometric stereo principle.

According to the present invention, for example there is provided an inspection apparatus including: an illumination section for illuminating an inspection target by a photometric stereo method; an imaging section for capturing an image of the inspection target illuminated by the illumination section; an inspection image generating section for obtaining a normal vector of the surface of the inspection target based on a plurality of luminance images acquired by the imaging section, to generate an inspection image made up of a plurality of pixel values in accordance with the normal vector; a display section for switching and displaying at least one of the plurality of luminance images and the inspection image, or simultaneously displaying at least one of the plurality of luminance images and the inspection image; an adjustment section for adjusting at least one of a control parameter of the imaging section and a control parameter of the illumination section; and an updating section for updating an image being displayed on the display section to an image where the control parameter has been reflected when the parameter is adjusted.

According to the present invention, a luminance image and an inspection image which is used for inspection are switched and displayed, or these are simultaneously displayed, thereby allowing the user to instinctively see a result of adjustment of a parameter. This can facilitate the setting of a parameter at the time of generating an inspection image from an image acquired by using a photometric stereo principle.

BRIEF DESCRIPTION OF THE DRAWINGS

FIG. 14 is a view showing one example of the user interface;

FIG. 22 is a view showing one example of the user interface;

DETAILED DESCRIPTION OF PREFERRED EMBODIMENT

Hereinafter, one embodiment of the present invention is shown. An individual embodiment described below will be useful for understanding a variety of concepts such as a superordinate concept, an intermediate concept, and a subordinate concept of the present invention. Further, a technical range of the present invention is defined by the claims, and is not limited by the following individual embodiment.

Figure 1:
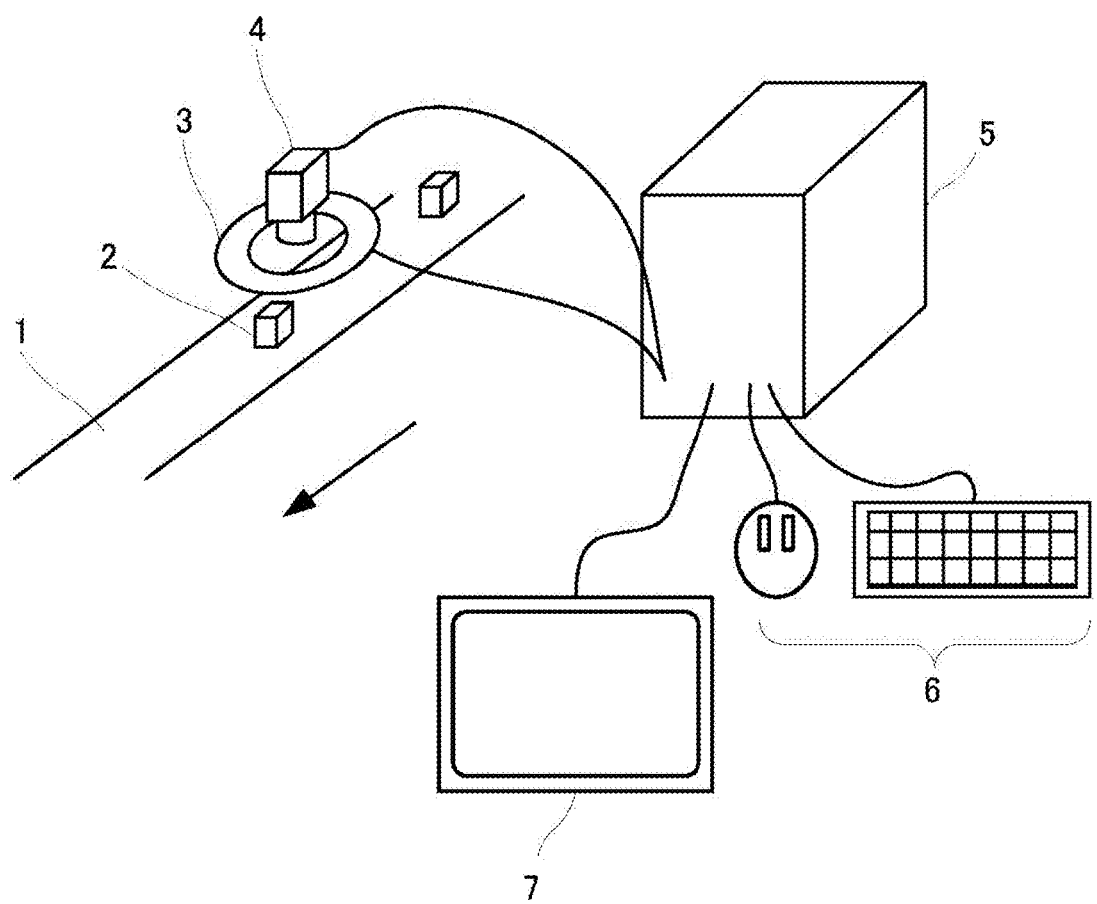
FIG. 1 is a view showing an outline of an inspection apparatus.

FIG. 1 is a view showing one example of a visual inspection system. A line 1 is a conveyer belt for conveying a workpiece 2 which is an inspection target. An illumination apparatus 3 is one example of an illumination section for illuminating an inspection target in accordance with a photometric stereo method. A camera 4 is one example of an imaging section for receiving reflective light from the illuminated inspection target to generate a luminance image in accordance with the photometric stereo method. An image processing apparatus 5 is a visual inspection apparatus for calculating a normal vector of the surface of the workpiece 2 from a plurality of luminance images acquired by the camera 4, performing accumulation computing of a pixel value of a pixel of interest by using a normal vector of a pixel adjacent to the pixel of interest with respect to an inclination image made up of pixel values based on the normal vector calculated from the plurality of luminance images and a reduced image of the inclination image, and generating an inspection image having the pixel value, to determine defectiveness/non-defectiveness of the inspection target by using the inspection image. The inclination image may be referred to as a normal vector image. The image processing apparatus 5 may create a reflectance image (albedo image) from the luminance image. A display part 7 displays a user interface for setting a control parameter related to inspection, an inclination image, a reflectance image, an inspection image, and the like. An input part 6 is a console, a pointing device, and a keyboard, and is used for setting a control parameter.

<Photometric Stereo Principle>

Figures 2A, 2B, 2C:
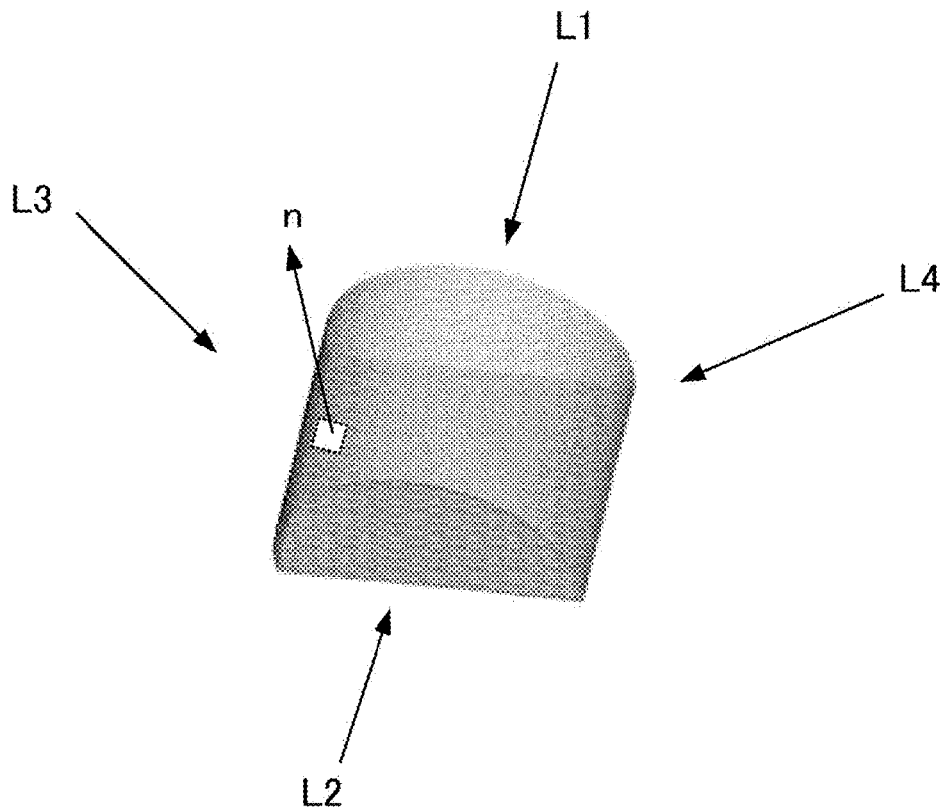
FIGS. 2A to 2C are views for describing a photometric stereo principle.

In a general photometric stereo method, as shown in FIG. 2A, illumination light L1 to illumination light L4 are applied to the workpiece 2 from four directions while being switched, to generate four luminance images. The direction of the illumination light used at the time of capturing each luminance image is in only one direction. Note that a luminance image is made up of a plurality of pixels, and four pixels whose coordinates match in the four luminance images correspond to the same surface of the workpiece. Expression 1 shown in FIG. 2B is established among pixel values (luminance values) I1, I2, I3, I4 of the four pixels and the normal vector n. Here, $\rho$ is a reflectance. L is a light amount of the illumination light from each direction, and is known. Here, the light amounts from the four directions are the same. S is an illumination-direction matrix, and is known. By solving this mathematical expression, the reflectance $\rho$ and the normal vector n for each coordinates (surface of the workpiece) are obtained. As a result, a reflectance image and an inclination image are obtained.

In the present embodiment, further, a height component is extracted from the inclination image to create, as the inspection image, a shape image showing a shape of the workpiece. The inspection image is obtained by an accumulation computing equation which is Expression 2 shown in FIG. 2C. Here, zn is a result of n-th accumulation, and shows the shape of the surface of the workpiece, x and y indicate coordinates of a pixel, and n shows how many times iteration calculation has been performed. Moreover, p shows an inclination component in a horizontal direction, q shows an inclination component in a vertical direction, p and q are obtained from the normal vector n, and w is weight. Further, a 1/1-inclination image is used in first accumulation computing, a 1/2-reduced inclination image is used in second accumulation computing, and a 1/4-reduced inclination image is used in third accumulation computing. At the time of creating the reduced image, reduction processing may be performed after Gaussian processing is performed.

In the present embodiment, a parameter called a characteristic size is adopted in the accumulation computing. The characteristic size is a parameter for giving weight to a component of a reduced image to be used in the accumulation computing. The characteristic size is a parameter showing a size of a surface shape of the workpiece 2. For example, when the characteristic size is 1, weight with respect to four pixels adjacent to a pixel of interest in an x-y direction is set the largest and the accumulation computing is performed. When the characteristic size is 2, weight with respect to eight pixels adjacent to the pixel of interest in the x-y direction is set the largest and the accumulation computing is performed. However, since computing using the eight pixels causes an increase in computing amount, the foregoing reduced image is created and used for the computing. That is, in place of using the eight adjacent pixels, the inclination image is reduced into 1/2 and the computing is performed. Thereby, concerning a certain pixel of interest, four pixels in the reduced image may be considered for the computing. Also when the characteristic size is increased to 4, 8, 16, and 32, reduced images corresponding thereto are created, and weight with respect to the reduced image corresponding to the characteristic size is set the largest, whereby a similar effect of reduction in computing load can be obtained.

Figure 3:
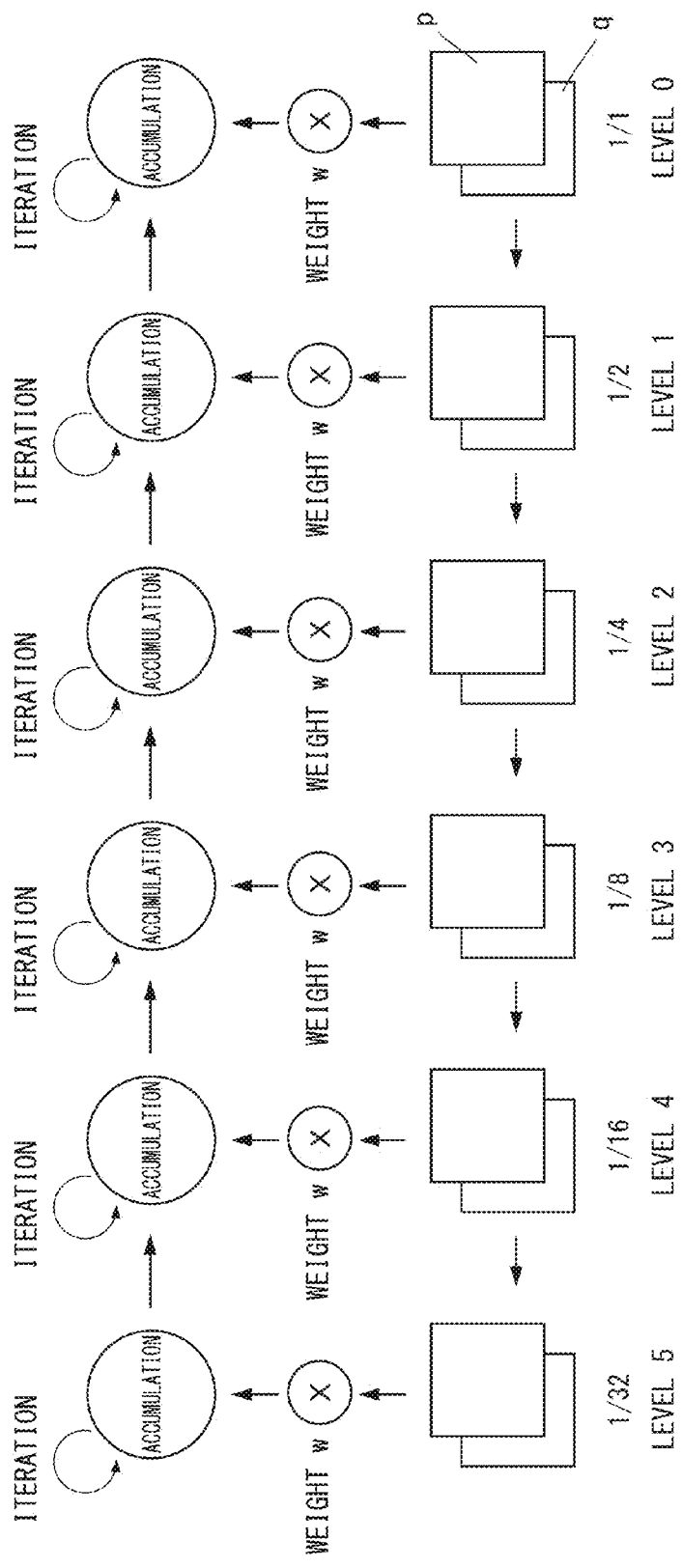
FIG. 3 is a diagram for describing accumulation computing.

FIG. 3 shows one example of the accumulation computing. In this example, two inclination images (an image with a horizontal inclination component p and an image with a vertical inclination component q) obtained from the normal vector n are inputted. First, a whole shape is accumulated by an inclination image with a large reduction degree, and a fine shape is accumulated by an image with a smaller reduction degree. This allows restoration of the whole shape in a short period of time. According to FIG. 3, for example, with respect to the 1/32-reduced image, z which is a parameter indicating the shape of the surface of the workpiece concerning the pixel of interest is calculated by Expression 2. The weight w is decided in accordance with the characteristic size. Each pixel constituting the reduced image is taken as a pixel of interest, and the accumulation computing is subjected to iteration (repetition processing). An initial value of z is zero. Then, z is calculated with respect to the 1/16-reduced image in accordance with Expression 2. Here, an inclination component of the 1/16 reduced image is accumulated on a result of the computing of 1/32. Similarly, the accumulation computing is performed from the 1/8-reduced image to the 1/1-image.

Figure 4:
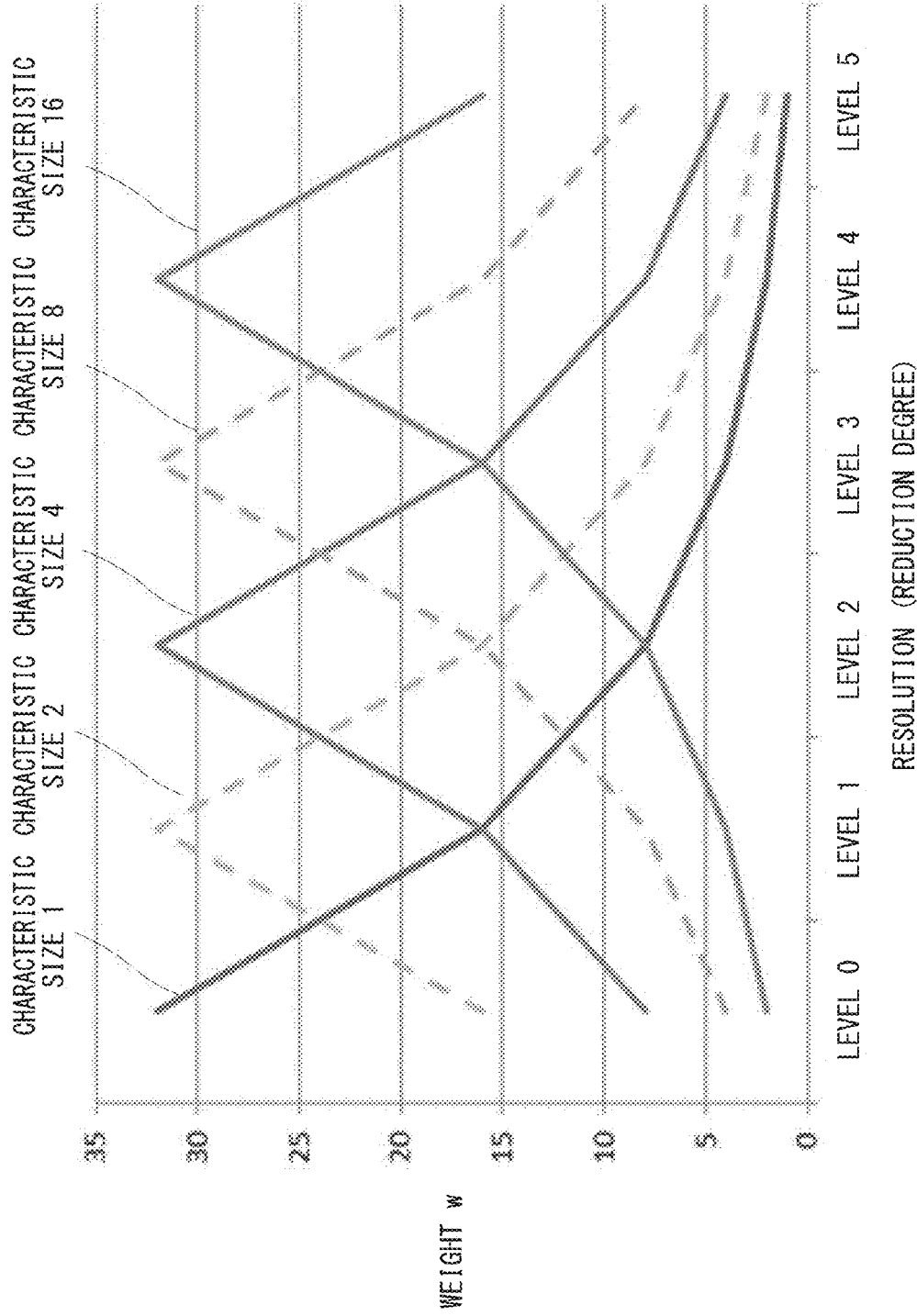
FIG. 4 is a diagram showing a method for deciding weight based on a characteristic size.

FIG. 4 shows one example of weight with respect to each characteristic size. A horizontal axis indicates a resolution level (reduction degree), and a vertical axis indicates weight. As can be seen from FIG. 4, in the characteristic size 1, weight is the largest at level 0 (1/1-image) with the smallest reduction degree. This allows accumulation of a finer shape. In the characteristic size 2, weight is the largest at level 1 (1/2-image). This allows further accumulation of a shape having a larger size. As thus described, each weight is decided such that a peak is generated at the level corresponding to the characteristic size.

As a method for restoring the shape image, other than the above accumulation computing, it is also possible to adopt known Fourier transform integration ("A Method for Enforcing Integrability in Shape from Shading Algorithms", IEEE Transactions on Pattern Analysis and Machine Intelligence, Vol. 10, No. 4 Jul. 1988). Also in this method, it is possible to change a characteristic size to be extracted by generating a reduced image in a calculation process and adjusting a weighting component.

Figure 5:
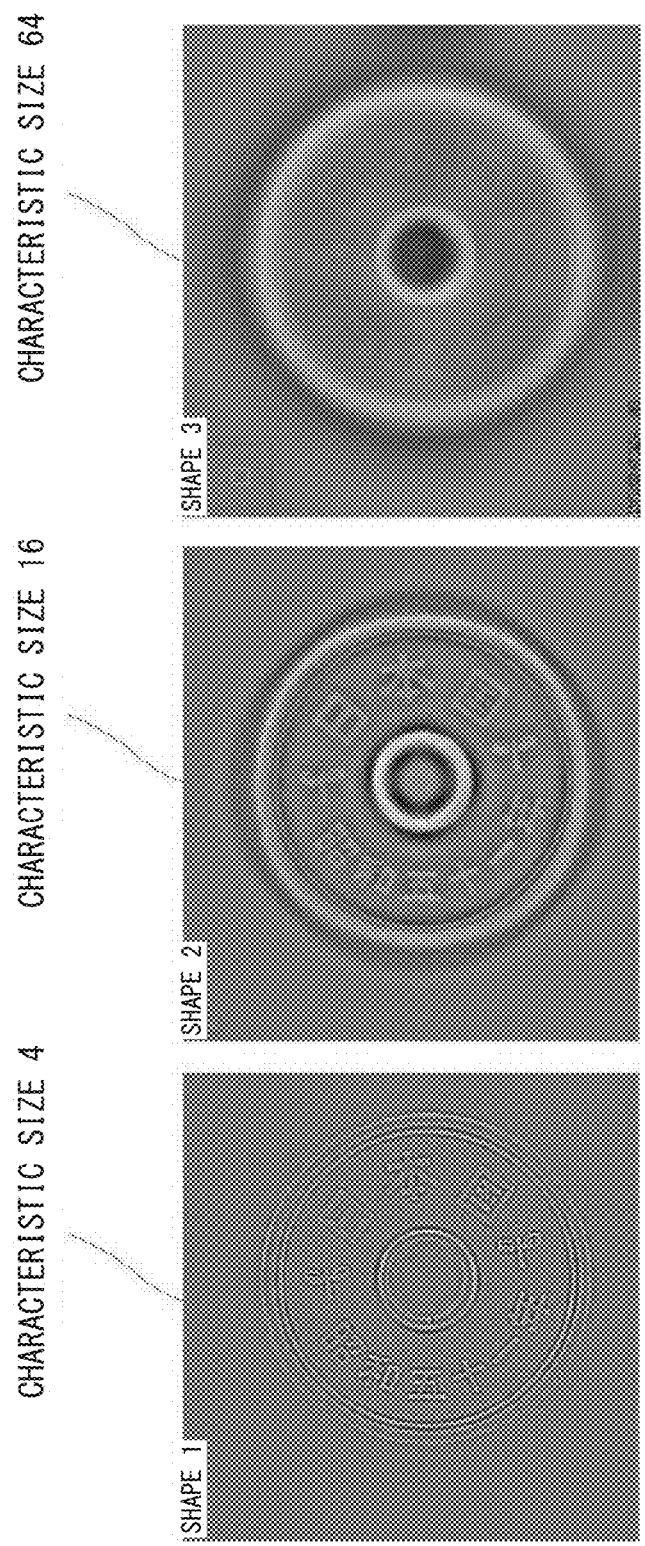
FIG. 5 is a view showing one example of inspection images with different characteristic sizes.

FIG. 5 shows one example of inspection images in accordance with differences in characteristic size. It can be seen that a fine shape is extracted in the characteristic size 4, a whole shape is extracted in the characteristic size 64, and a shape of an intermediate size therebetween is extracted in the characteristic size 16. In such a manner, a small characteristic size is useful for inspecting a fine flaw, a large characteristic size is suitable for discriminating the presence or absence of an object, and an intermediate characteristic size is suitable for OCR of an uneven character, and the like. That is, selecting a suitable characteristic size in accordance with the inspection tool can improve the inspection accuracy.

Figure 6:
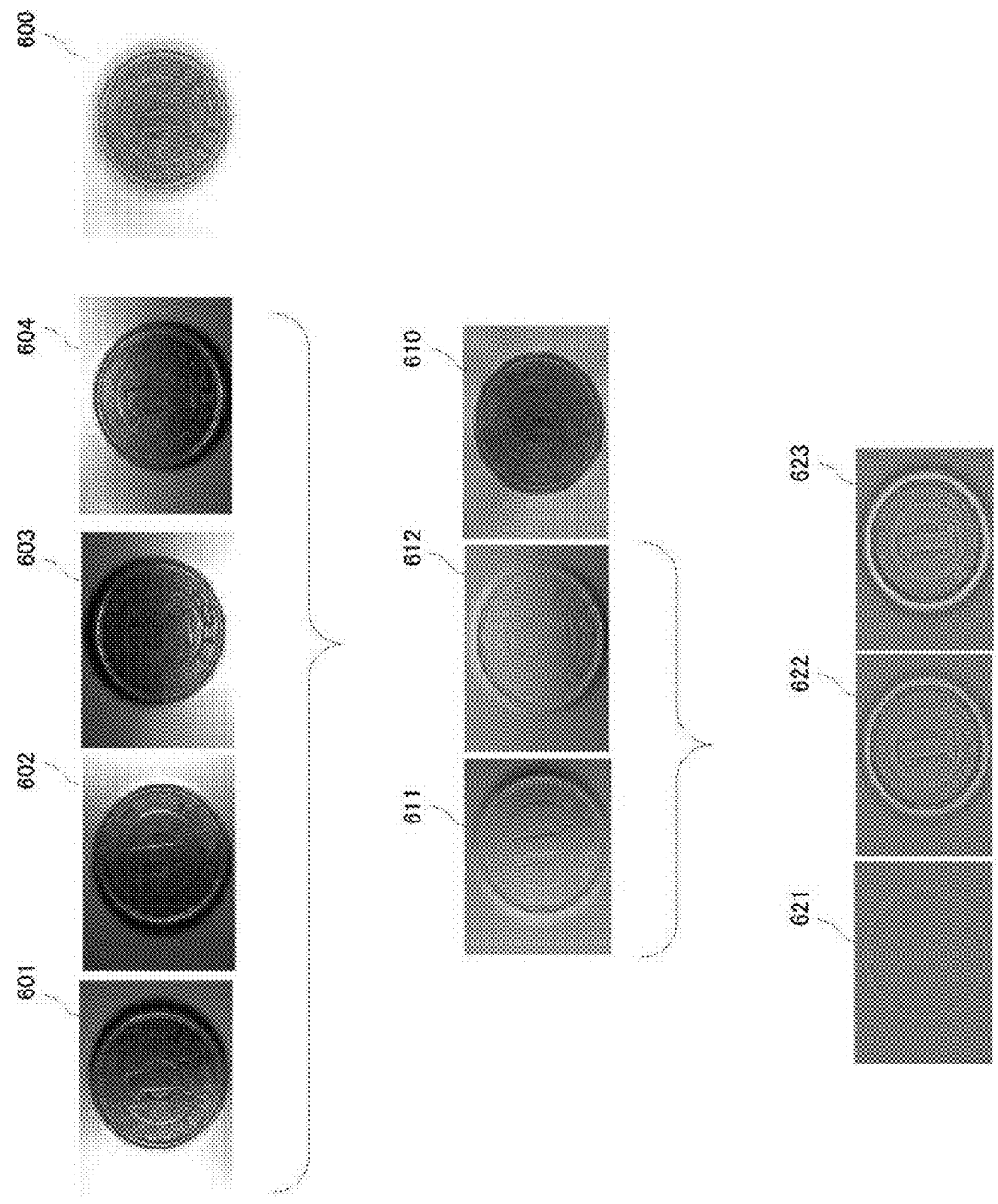
FIG. 6 is a view describing images related to generation of a shape image.

FIG. 6 is a view showing a step of creating an inspection image by the photometric stereo method. Luminance images 601 to 604 are luminance images acquired by illuminating the workpiece 2 with illumination light from respectively different illumination directions. Note that a luminance image 600 is a luminance image obtained by simultaneously illuminating the workpiece 2 from four directions. A normal vector of the surface of the workpiece is obtained by computing from the plurality of luminance images acquired by illuminating the workpiece 2 with the illumination light from the respectively different illumination directions. An inclination image 611 is an inclination image whose pixel value is an inclination component in an x-direction of the normal vector obtained from the luminance images 601 to 604. An inclination image 612 is an inclination image whose pixel value is an inclination component in a y-direction of the normal vector obtained from the luminance images 601 to 604. A reflectance image 610 is a reflectance image obtained by removing an amount of change in luminance value due to inclination of the surface of the workpiece from the normal vector obtained from the luminance images 601 to 604, to form an image with a reflectance of the surface of the workpiece. Inspection images 621 to 623 are images with respectively different characteristic sizes obtained from the inclination images 611, 612. Each of the inspection images 621 to 623 is also made up of pixels based on an inclination component, and is thus a type of the inclination image. In such a procedure, the inspection image of the workpiece 2 is generated. Note that the luminance image 600 or the reflectance image 610 as an all-directional illumination image may be adopted as the inspection image, depending on the inspection tool. The all-directional illumination image is a luminance image acquired by lighting all of a plurality of light sources provided in the illumination apparatus 3.

<Texture Information>

Figure 7:
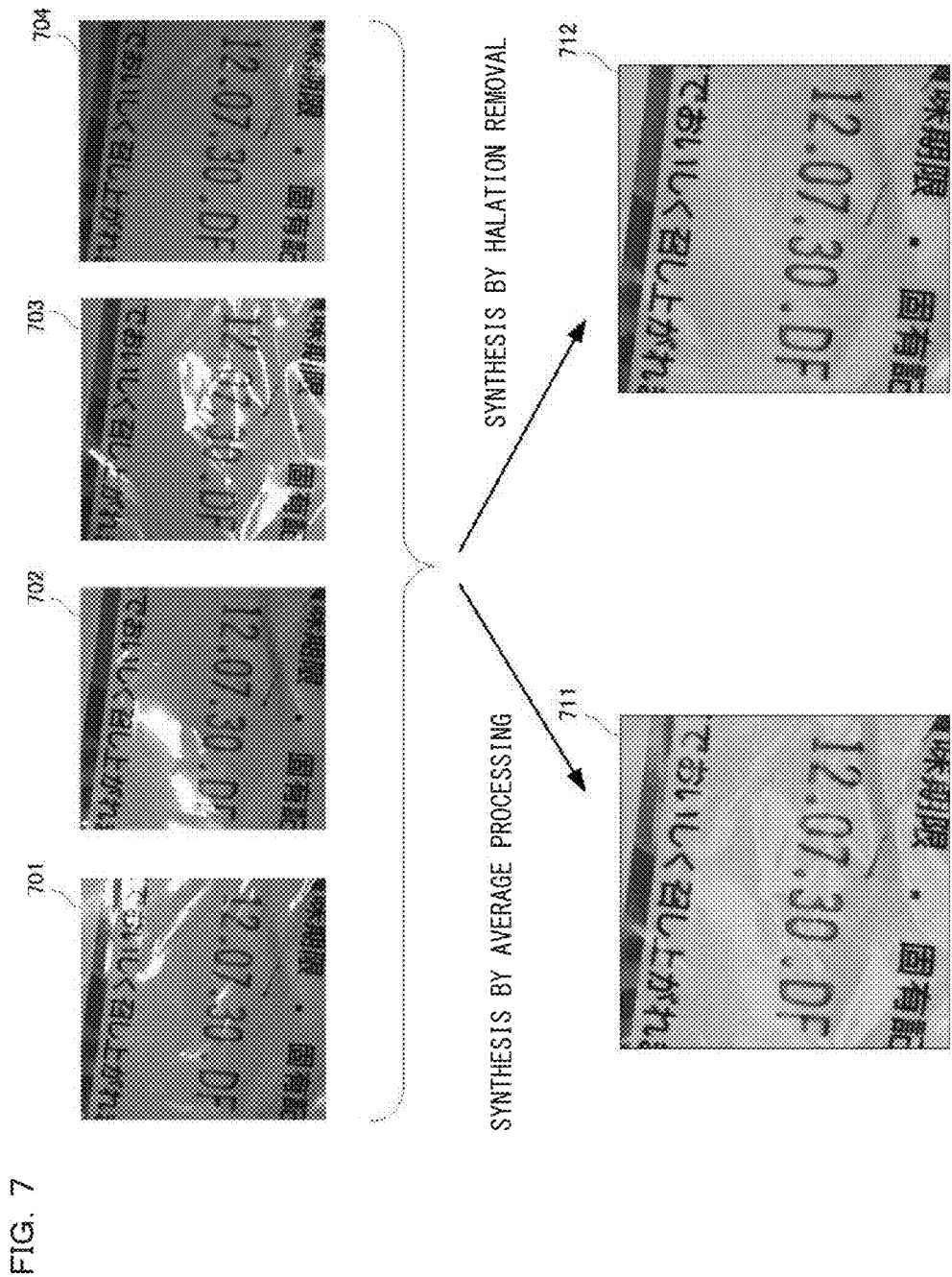
FIG. 7 is a view describing a method for generating a texture image.

Texture information is information based on the reflectance ρ of the surface of the workpiece 2. The reflectance ρ is obtained by Expression 1, namely, one reflectance image is obtained from four luminance images. The reflectance image is an image having a pixel value proportional to the reflectance ρ of the surface of the workpiece. As shown in FIG. 7, a normal vector is calculated from four luminance images 701 to 704, and based on the calculated normal vector and a luminance value of a pixel corresponding to each of the plurality of luminance images, a pixel value proportional to a reflectance of each pixel is calculated, to obtain texture images 711, 712 which are reflectance images. Examples of this generation method includes a method of averaging pixels of the four luminance images to obtain a texture image, and a method of removing halation from the four luminance images and then averaging pixels to obtain a texture image. The texture image 711 is one example of the image obtained by averaging pixels, and the texture image 712 is one example of the image obtained by removing halation. In the four luminance images, four pixels whose coordinates match exist. It is possible to remove halation by removing a pixel with the largest pixel value out of the four pixels, or by removing pixels with the largest to N-th largest pixel values (N is a natural number not larger than 3). This is because halation appears as high luminance in the image. Both the texture images 711, 712 are made up of pixels based on the reflectance, and are thus types of the reflectance image.

<Function Block>

Figure 8:
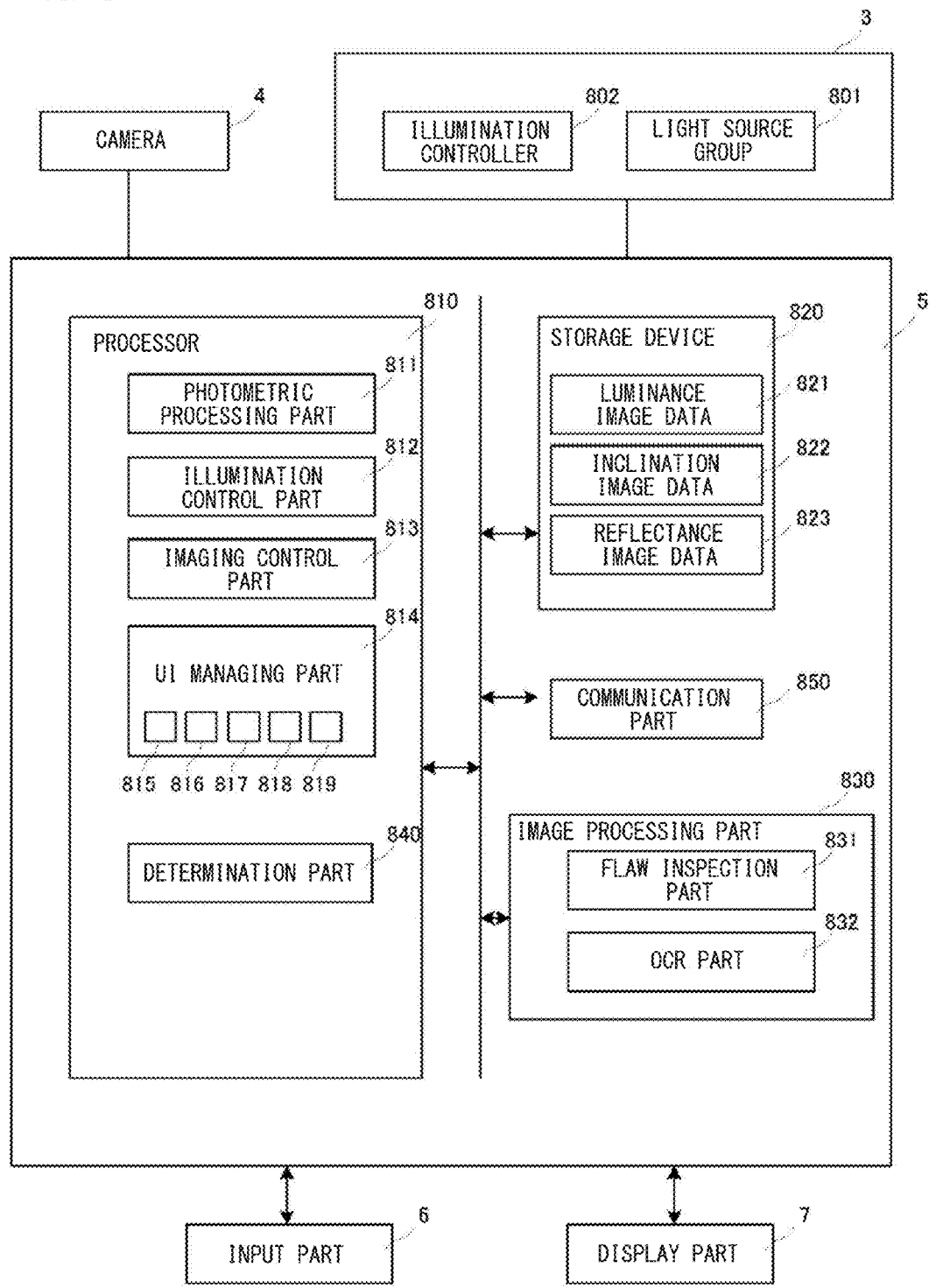
FIG. 8 is a function block diagram of the inspection apparatus.

FIG. 8 is a block diagram of the inspection apparatus. In this example, the illumination apparatus 3, the camera 4, and the image processing apparatus 5 are respectively housed in separate housings, but this is merely an example, and the illumination apparatus 3, the camera 4, and the image processing apparatus 5 may be integrated as appropriate. The illumination apparatus 3 is one example of the illumination section for illuminating the inspection target in accordance with the photometric stereo method, and provided with a light source group 801 and an illumination controller 802 for controlling this light source group. One segment may be formed of a plurality of light-emitting elements, and the light source group 801 may be formed of a plurality of segments. The number of segments is generally four, but may be any number as long as it is not smaller than three. This is because an inspection image can be generated by the photometric stereo method if the workpiece 2 can be illuminated from three or more illumination directions. As shown in FIG. 1, an outer shape of the illumination apparatus 3 may be a ring shape. Further, the illumination apparatus 3 may be configured by a plurality of illumination units each separated from one another. For example, although illumination units that are used for capturing an image of the workpiece 2 exist in the market, these illumination units are not developed for photometric stereo. However, the illumination apparatus 3 may be configured by preparing a plurality of such illumination units and connecting an illumination controller for controlling these illumination units. The illumination controller 802 controls lighting timing and a lighting pattern of the light source group 801 in accordance with a control command from the image processing apparatus 5. Although a description will be given assuming that the illumination controller 802 is incorporated in the illumination apparatus 3, the illumination controller 802 may be incorporated in the camera 4 or in the image processing apparatus 5, or may be housed in a housing independent of these.

The camera 4 is one example of the imaging section for receiving reflective light from the illuminated inspection target to generate a luminance image in accordance with the photometric stereo method, and performs the imaging processing in accordance with a control command from the image processing apparatus 5. The camera 4 may create a luminance image of the workpiece 2 and transmit the luminance image to the image processing apparatus 5, or the camera 4 may transmit a luminance signal obtained from an imaging element to the image processing apparatus 5 and the image processing apparatus 5 may generate a luminance image. Since the luminance signal is a signal used for generating the luminance image, the luminance signal is also the luminance image in a broad sense.

The image processing apparatus 5 is one type of computer, and has a processor 810 such as a CPU and an ASIC, a storage device 820 such as a RAM, a ROM, and a portable storage medium, an image processing part 830 such as an ASIC, and a communication part 850 such as a network interface. The processor 810 serves to set an inspection tool, adjust a control parameter, and generate/regenerate/update an inspection image. A photometric processing part 811 functions as a computing section (inspection image generating section) for calculating the normal vector n of the surface of the workpiece 2 from a plurality of luminance images acquired by the camera 4, and performing accumulation computing of a pixel value of a pixel of interest by using the normal vector n of a pixel adjacent to the pixel of interest with respect to an inclination image having a pixel value based on the normal vector n calculated from the plurality of luminance images and a reduced image of the inclination image, to generate an inspection image having the pixel value. Note that, specifically, the inspection image is generated by using the foregoing mathematical expression or the like. An illumination control part 812 transmits a control command to the illumination controller 802 to control an illumination pattern, illumination switching timing, or the like. An imaging control part 813 controls the camera 4. A UI managing part 814 displays on the display part 7 a user interface (UI) for setting an inspection tool, a UI for setting a parameter required for generating an inspection image, and the like, and sets the inspection tool and the parameter in accordance with information inputted from the input part 6. In particular, a characteristic size setting part 815 functions as a setting section for setting a characteristic size which is a parameter for giving weight w to a component of a reduced image that is used in the accumulation computing. An image selection part 816 selects an image to be displayed, or the like, out of a plurality of luminance images, a plurality of inspection images, a plurality of inclination images and a plurality of reflectance images. The image selection part 816 may select an image, which is to be saved or outputted, out of the plurality of luminance images acquired by the camera 4 and the inspection image. An inspection tool setting part 817 sets an inspection tool for the inspection image selected by the image selection part 816. A reference image setting part 818 sets a reference image acquired from a non-defective product. A display control part 851 switches and displays the luminance image and the inspection image on the display part 7, or simultaneously displays the luminance image and the inspection image. Further, when the control parameter is adjusted, the display control part 851 updates the image being displayed on the display part 7 to an image where the control parameter has been reflected. An inspection tool setting part 817 may include the display control part 851, the characteristic size setting part 815, the image selection part 816, the reference image setting part 818, and a condition setting part 819. The image processing part 830 functions as an inspection region setting section for executing search processing such as a pattern search on an inspection image by using the reference image, to set an inspection region in the inspection image. The inspection region is, for example, a character recognition region. The condition setting part 819 sets a condition for outputting an image to an external device connected to the display part 7 or the communication part 850, or sets a condition for saving an image into a portable storage medium. A determination part 840 functions as a determination section for determining defectiveness/non-defectiveness of the workpiece 2 by using the inspection image. For example, the determination part 840 receives a result of the inspection executed in the image processing part 830 by using the inspection image and determines whether or not the inspection result satisfies a non-defective product condition (tolerance or the like).

The storage device 820 stores luminance image data 821 which is data of the luminance image acquired by the camera 4, and inclination image data 822 and reflectance image data 823 generated by the photometric processing part 811. Further, the storage device 820 also stores a variety of setting data, a program code for generating a user interface, and the like. The storage device 820 may store and hold inspection images with respectively different characteristic sizes. Further, in addition to the inspection image, the storage device 820 may also store inclination image data or reflectance image data used for generating the inspection image. When erroneous determination on the workpiece 2 is found, these pieces of data may be useful for specifying which of the inspection image, the inclination image, and the reflectance image has a problem and correcting its control parameter.

The image processing part 830 executes visual inspection by using the inspection image (the inclination image data 822, the reflectance image data 823) generated by the photometric processing part 811. A flaw inspection part 831 executes flaw inspection on a plurality of inspection images generated by using respectively different characteristic sizes. An OCR part 832 functions as a character recognition processing section for performing character recognition processing on a plurality of inspection images generated by using respectively different characteristic sizes. The flaw inspection part 831 and the OCR part 832 may read the inspection image (the inclination image data 822, the reflectance image data 823) stored in the storage device 820 and execute inspection, to write an inspection result into the storage device 820 or to pass the inspection result to the determination part 840. The determination part 840 determines defectiveness/non-defectiveness of the workpiece 2 based on this inspection result.

<Setting Mode>

The inspection system has a setting mode for setting an inspection tool and an inspection mode (operation mode) for executing a visual inspection of the workpiece 2 in accordance with the set inspection tool. Here, one example of the setting mode will be described.

Figure 9:
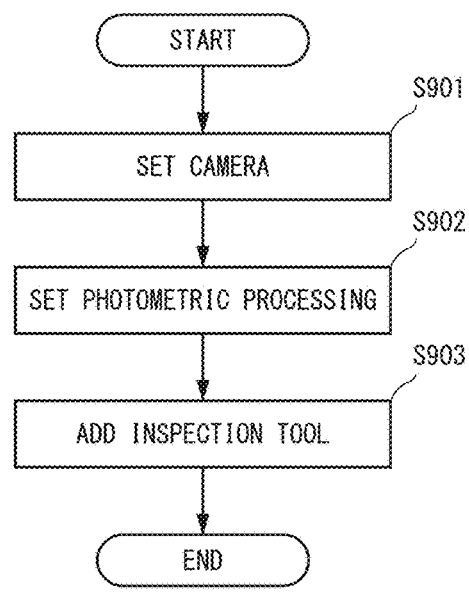
FIG. 9 is a flowchart showing a setting mode.

FIG. 9 is a flowchart concerning the setting mode. When the start of the setting mode is designated through the input part 6, the UI managing part 814 of the processor 810 displays a UI for setting the inspection tool on the display part 7.

Figure 10:
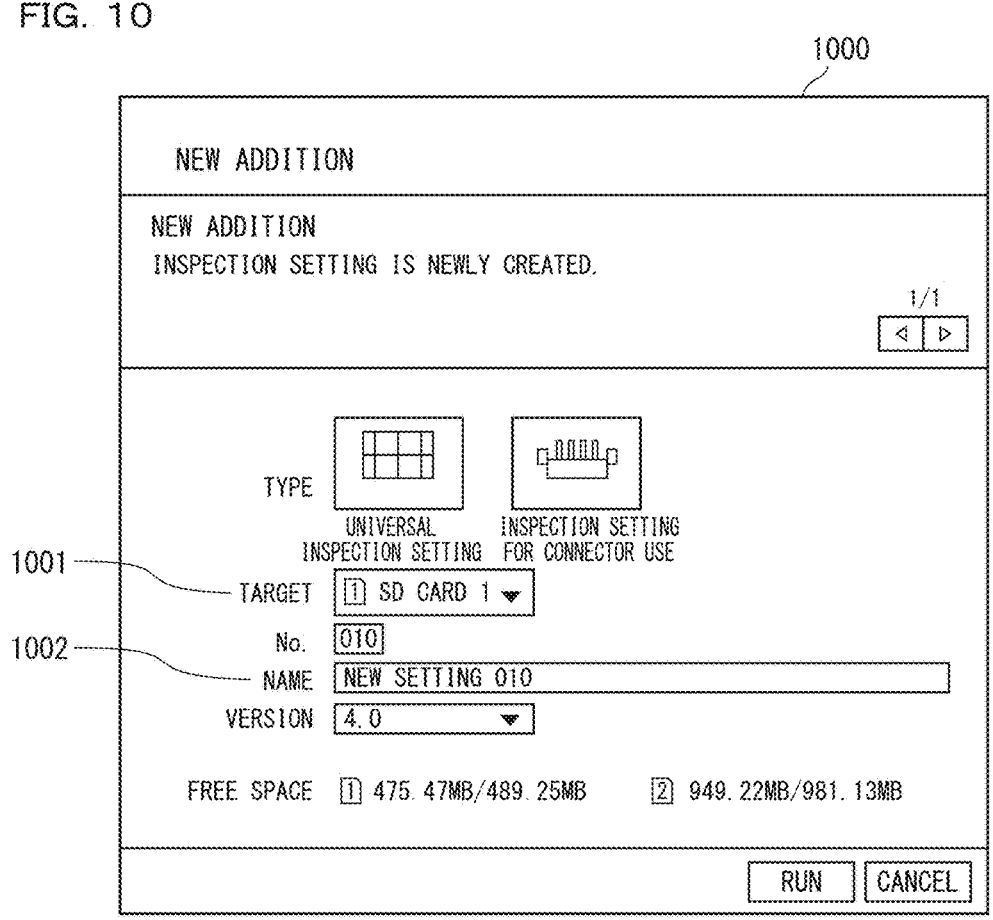
FIG. 10 is a view showing one example of a user interface.

FIG. 10 shows one example of the UI. A UI 1000 displayed on the display part 7 by the UI managing part 814 is provided with a pull-down menu 1001 for designating a saving destination of an inspection result, and a text box 1002 for inputting a name of the inspection tool. When detecting pressing-down of a run button, the UI managing part 814 displays the next UI.

Figure 11:
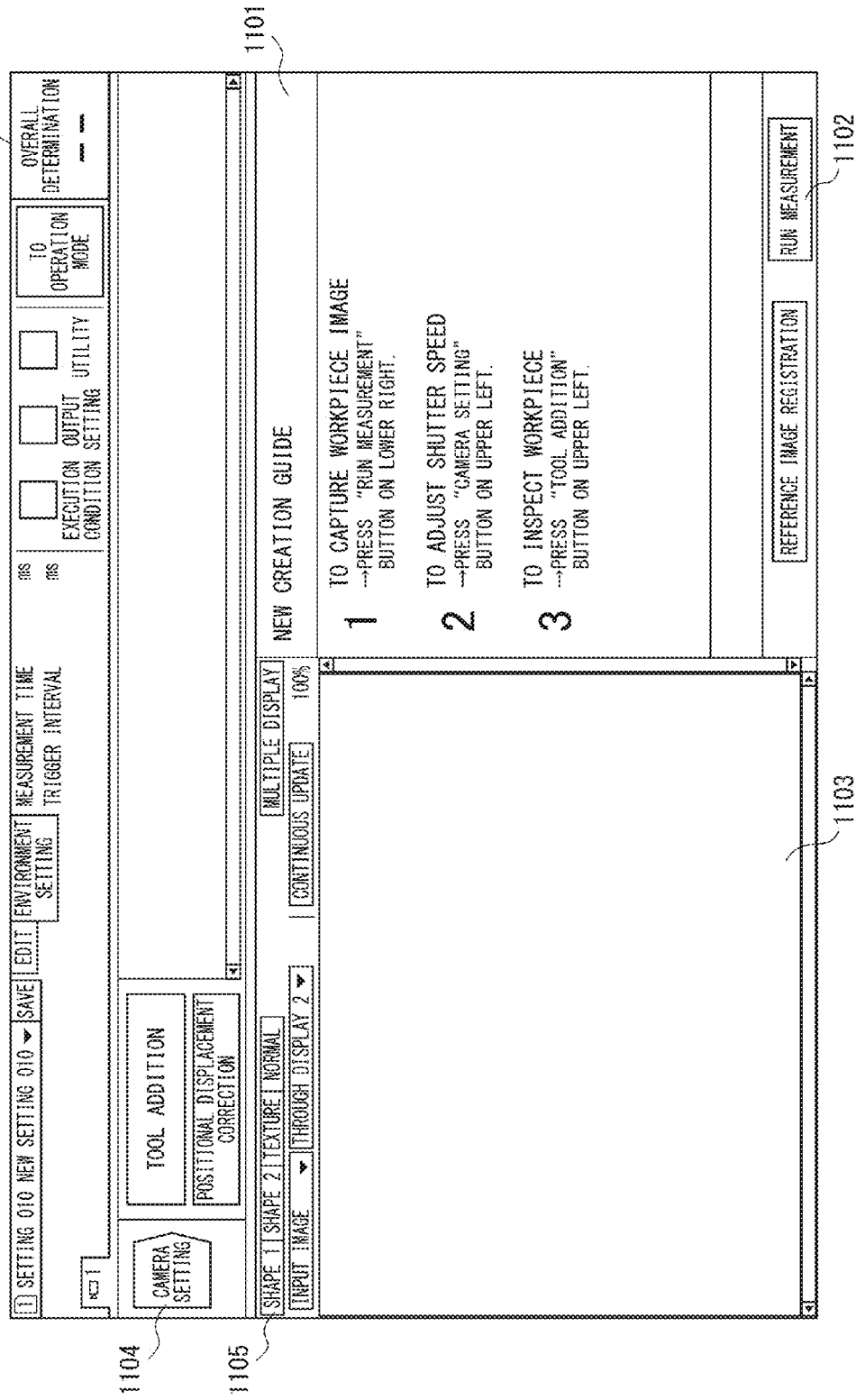
FIG. 11 is a view showing one example of the user interface.

A UI 1100 shown in FIG. 11 has guidance 1101 for setting the inspection tool, a measurement run button 1102 for designating the camera 4 to perform imaging, a display region 1103 for displaying an image captured by the camera 4, and a camera setting button 1104 for designating the start of setting of the camera. An image selection part 1105 is a button for selecting an image to be displayed in the display region 1103 or an image to be used for the inspection. In this example, any one image out of a shape 1, a shape 2, a texture, and normal is optionally selected by the image selection part 1105. When the measurement run button 1102 is operated, the imaging control part designates the camera 4 to perform imaging. The UI managing part 814 renders a luminance image acquired by the camera 4 to the display region 1103. Note that, when another image is selected by the image selection part 1105, the UI managing part 814 renders the image selected by the image selection part 1105 to the display region 1103. As thus described, the user can switch an image displayed in the display region 1103 by operating the image selection part 1105 or designating switching of the image through the input part 6. When the camera setting button 1104 is operated, the UI managing part 814 performs switching to the next UI.

Figure 12:
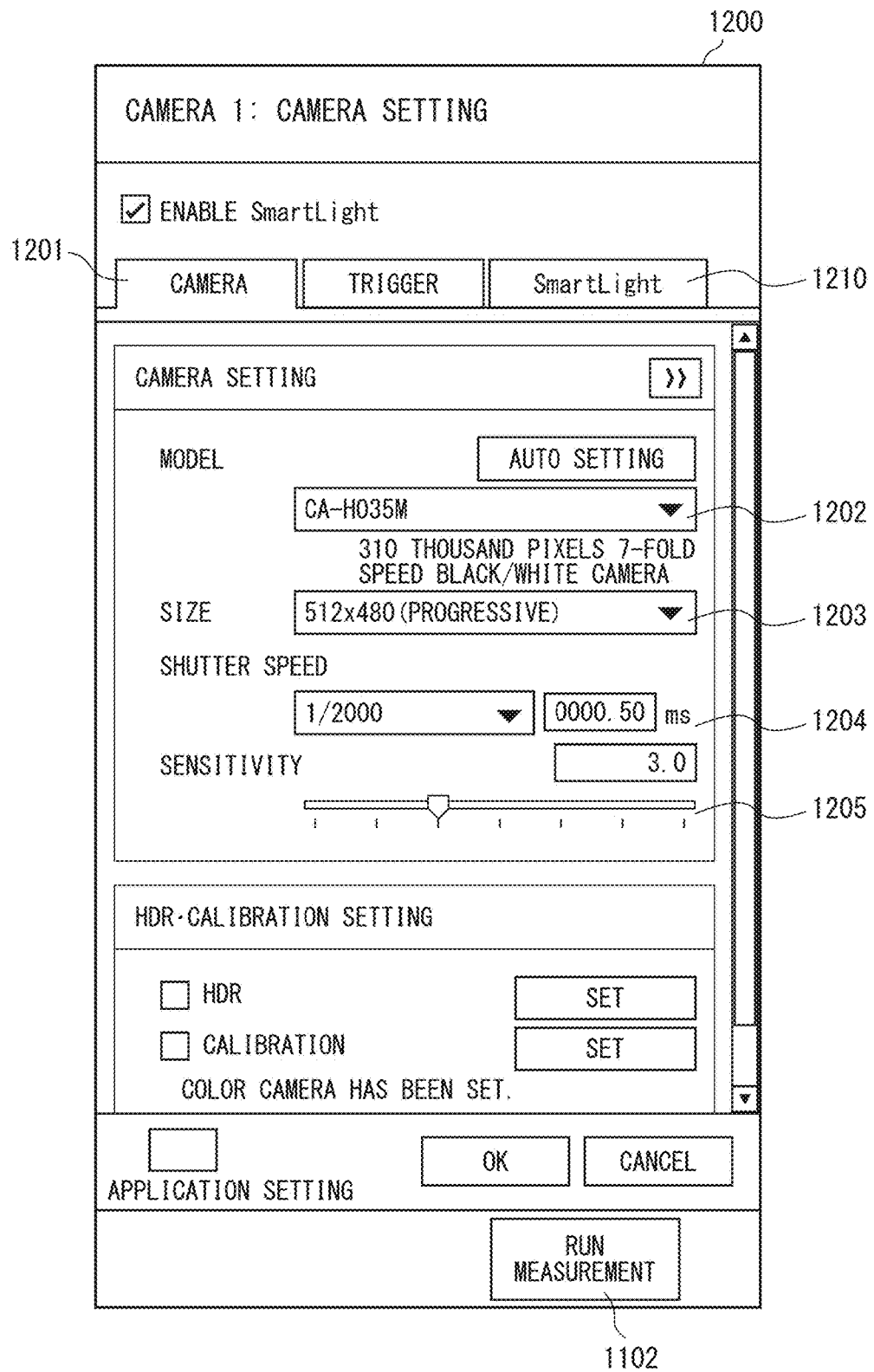
FIG. 12 is a view showing one example of the user interface.

In S901, the UI managing part 814 displays a UI for setting the camera 4 on the display part 7, to execute setting of the camera. FIG. 12 shows one example of a camera setting UI 1200. A camera setting tab 1201 has a pull-down menu 1202 for setting a model of a camera, a pull-down menu 1203 for setting an image size, a pull-down menu 1204 for setting a shutter speed, and a slider 1205 for setting the sensitivity of the camera. When the measurement run button 1102 is operated, the UI managing part 814 displays in the display region 1103 a luminance image acquired by the camera 4 in accordance with an imaging parameter set at that point. Hence, it is possible to determine whether or not the set parameter is suitable.

Figure 13:
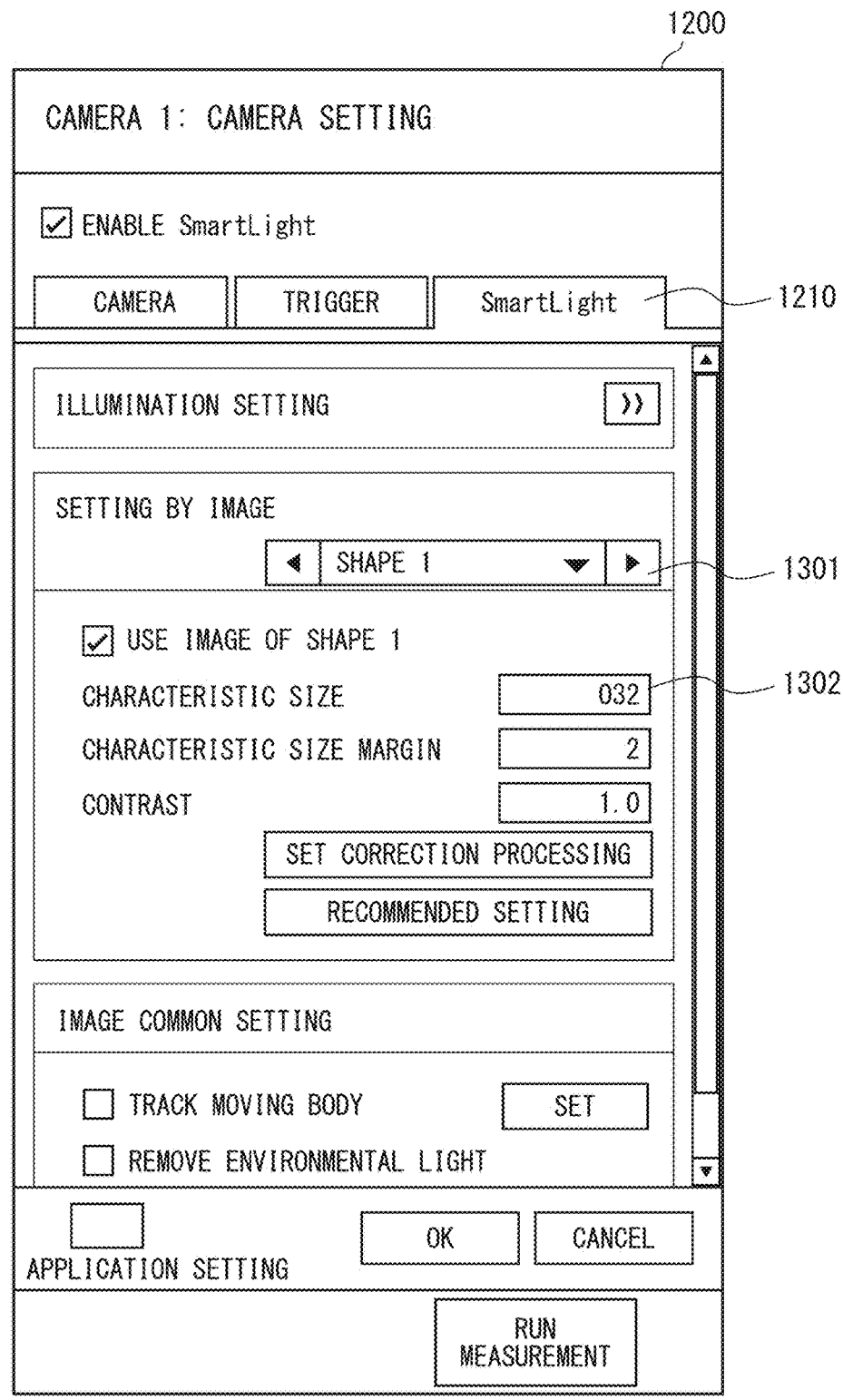
FIG. 13 is a view showing one example of the user interface.

In S902, the UI managing part 814 displays a UI for setting photometric processing on the display part 7, to execute the setting. For example, when detecting that a photometric stereo setting tab 1210 provided in the camera setting UI 1200 is operated, the UI managing part 814 switches the photometric stereo setting tab 1210 to be enabled, as shown in FIG. 13. Switching the photometric stereo setting tab 1210 to be enabled means switching a display state of the photometric stereo setting tab 1210 to a user operable state. The photometric stereo setting tab 1210 includes a pull-down menu 1301 for selecting an image and a characteristic size setting part 1302. In this example, it is assumed that any of three inspection images (shape 1, shape 2, shape 3) with respectively different characteristic sizes can be selected. A characteristic size is set by the characteristic size setting part 1302 for each image selected by the pull-down menu 1301.

A selection part for selecting an illumination pattern may be arranged in the photometric stereo setting tab 1210. Further, a designation part for designating an amount of emission for one illumination may be provided.

Figure 14:
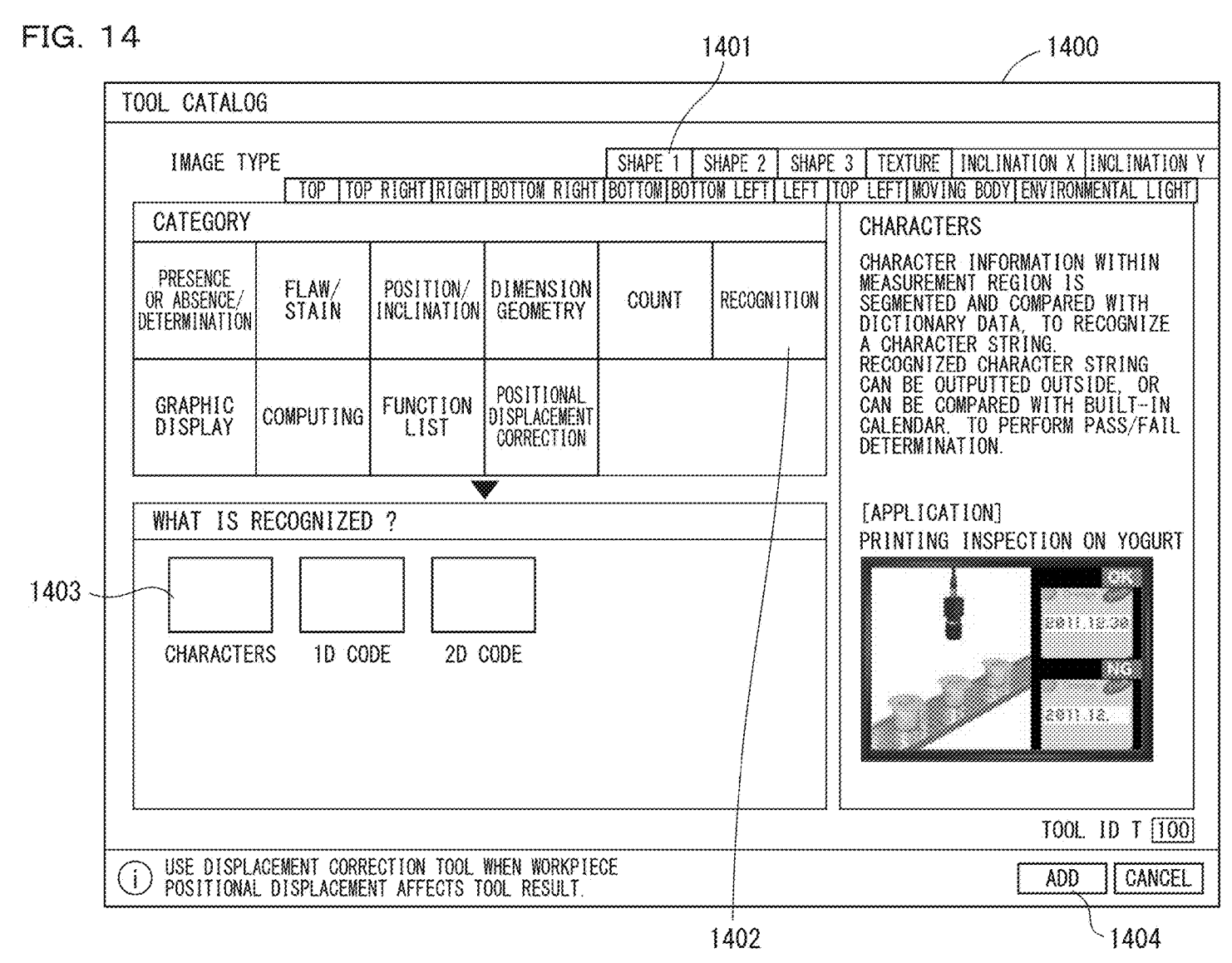
Figure 15:
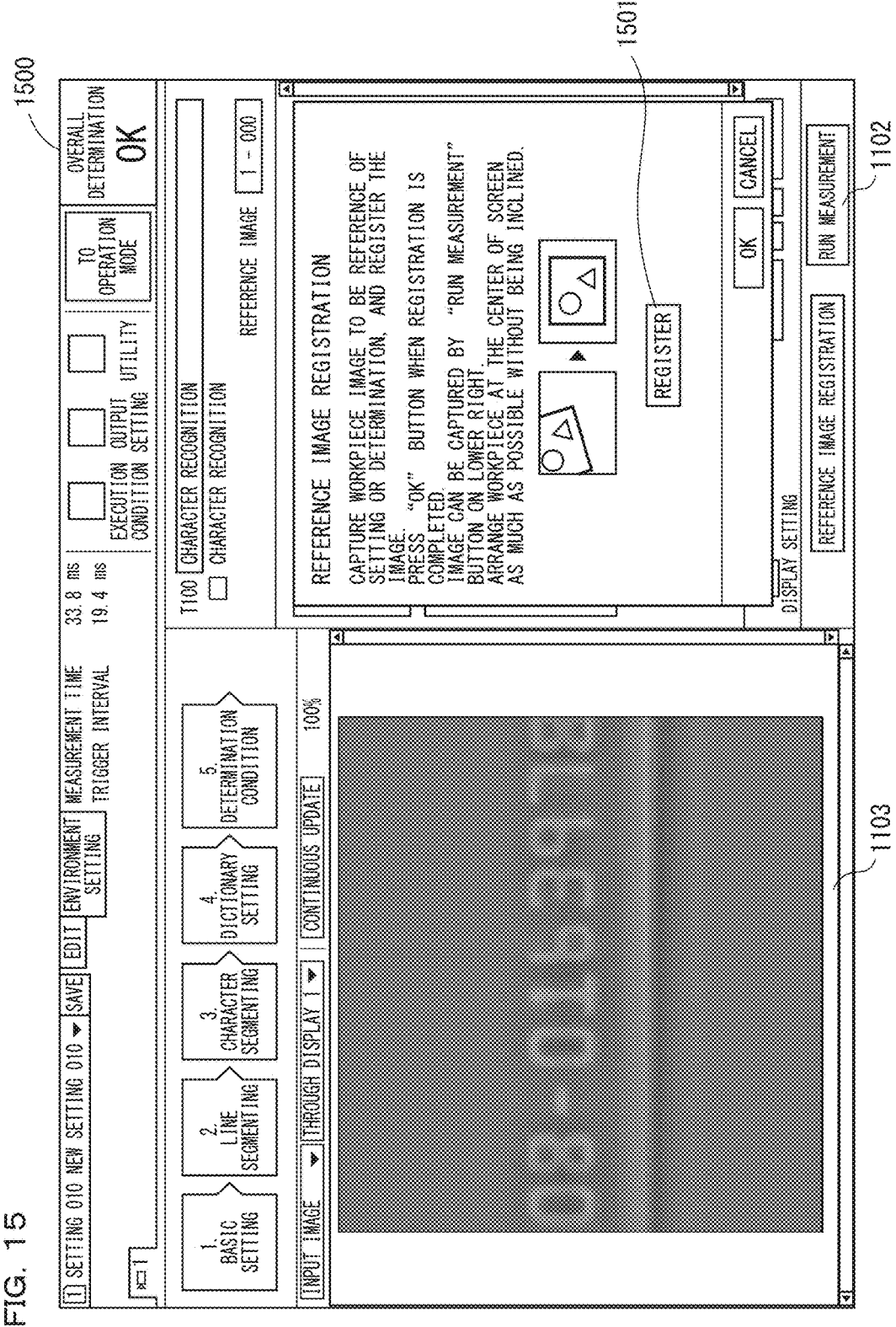
FIG. 15 is a view showing one example of the user interface.

In S903, the UI managing part 814 displays a UI for setting the inspection tool on the display part 7, to execute the setting. FIG. 14 is one example of a UI 1400 for setting the inspection tool. An image selection button 1401 is a button for selecting an inspection image to be used for inspection out of a plurality of inspection images. An inspection category selection button 1402 is a button for selecting a category of a tool to be added as the inspection tool out of a plurality of inspection categories. A recognition target setting button 1403 is a button for selecting one out of a plurality of recognition targets. In this example, "shape 1" is selected as the inspection image, "recognition" is selected as the category, and "character recognition" is selected as the recognition processing. When an addition button 1404 is operated, the UI managing part 814 performs switching to the next UI. FIG. 15 shows a reference image registration UI 1500. The reference image registration UI 1500 is provided with a registration button 1501 in addition to the measurement run button 1102 and the display region 1103 described above. When the registration button 1501 is operated, the UI managing part 814 registers as the reference image an image acquired by the measurement run button 1102 and displayed in the display region 1103. When the registration is completed, the UI managing part 814 performs switching to the next UI.

Figure 16:
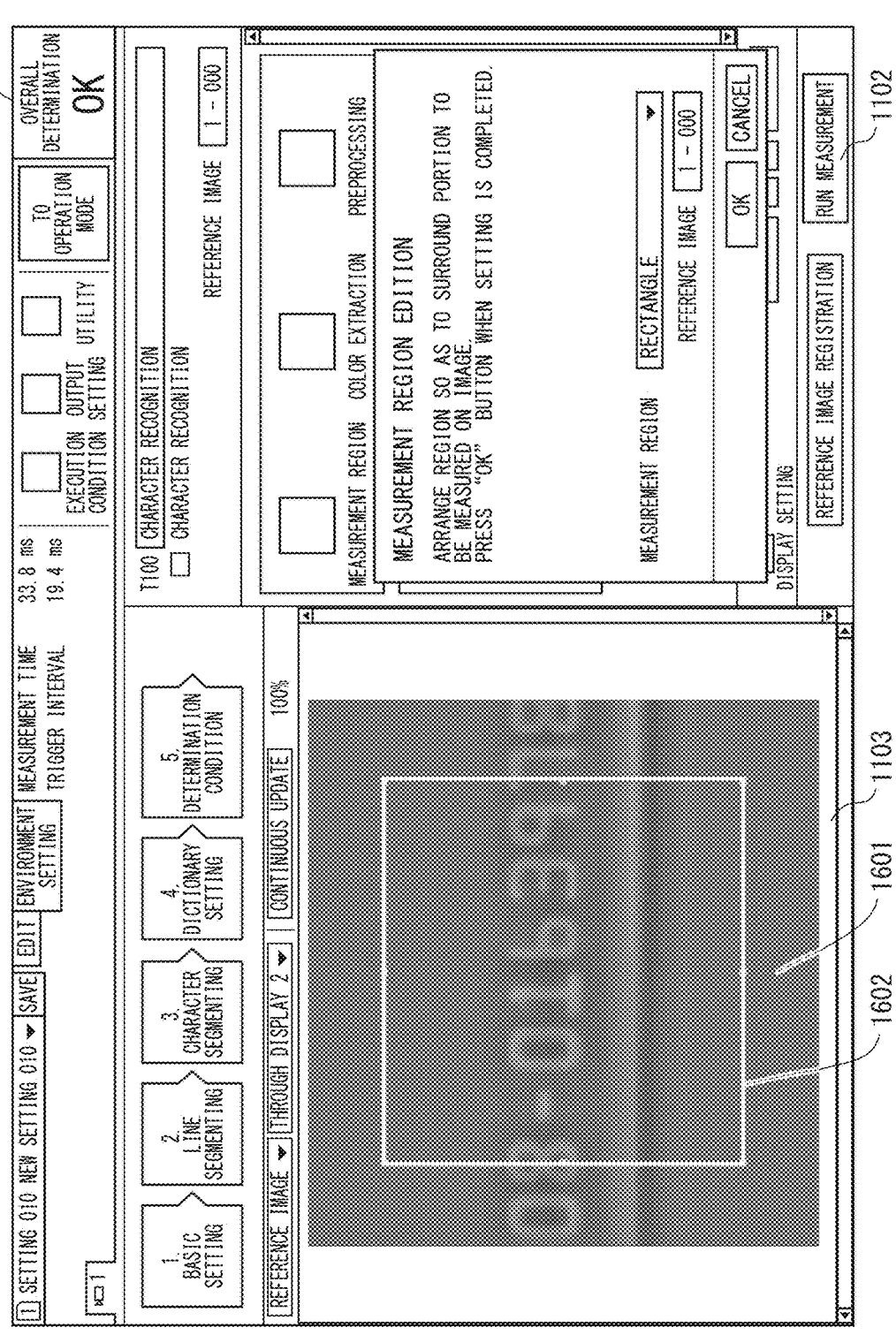
FIG. 16 is a view showing one example of the user interface.

FIG. 16 shows a measurement region setting UI 1600. The display region 1103 of the measurement region setting UI 1600 is provided with a reference image 1601 and a frame 1602 showing a measurement region. The UI managing part 814 changes a position and a size of the frame 1602 in accordance with designation from the input part 6. The user adjusts the position and the size of the frame 1602 in accordance with a position and a size of a portion to be measured in the reference image 1601. The UI managing part 814 further executes character segmenting setting, or dictionary setting for registering a specific example (character image) of a character to be recognized, a character corresponding to the character image, and the like.

Figure 17:
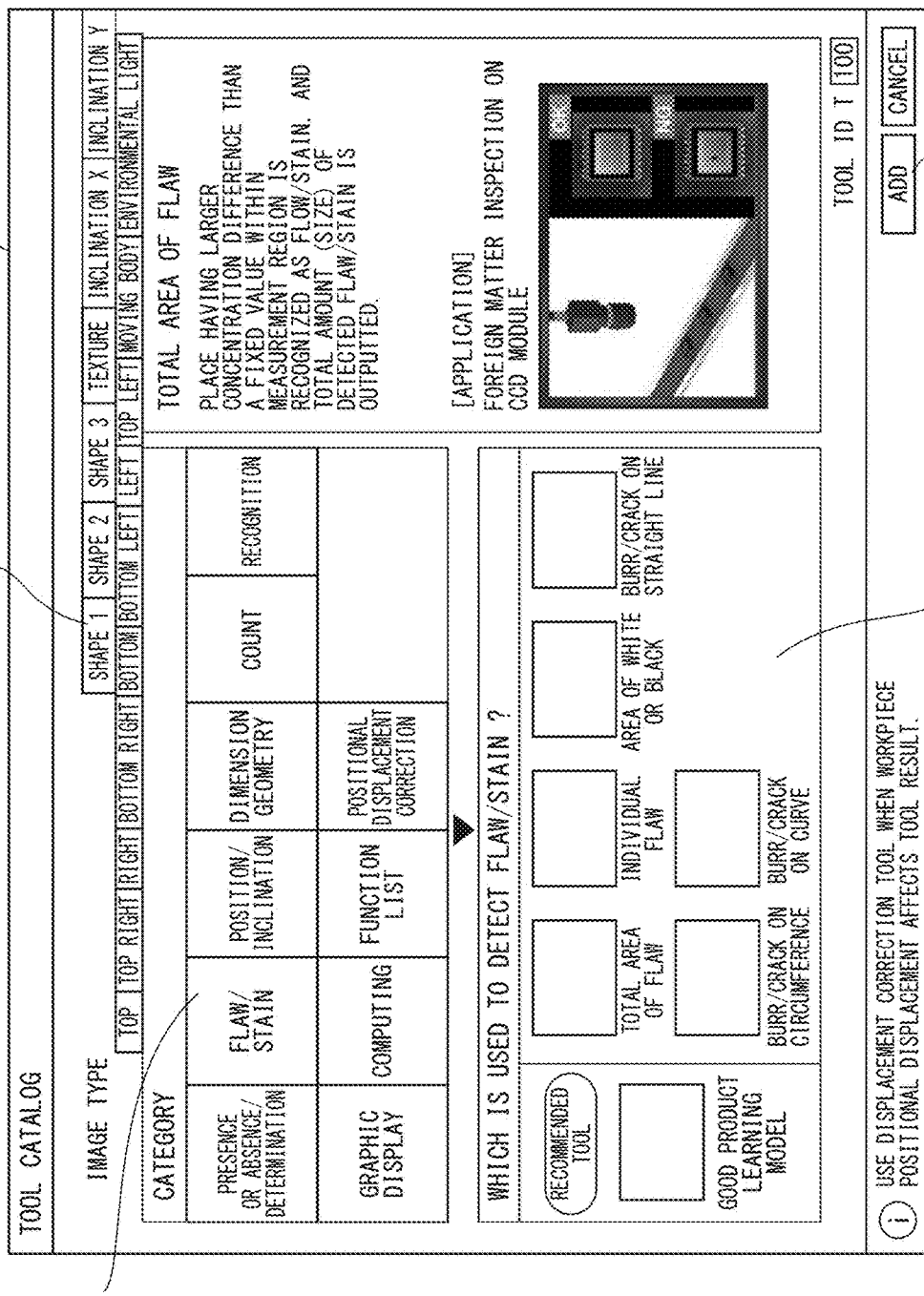
FIG. 17 is a view showing one example of the user interface.

Next, a flaw inspection tool will be described. As shown in FIG. 17, when the flaw inspection is selected by the inspection category selection button 1402, the UI managing part 814 displays an inspection content selection button 1701. In this example, a tool for measuring a total area of a flaw has been selected by the inspection content selection button 1701. When the addition button 1404 is operated, the UI managing part 814 switches the UI.

Figure 18:
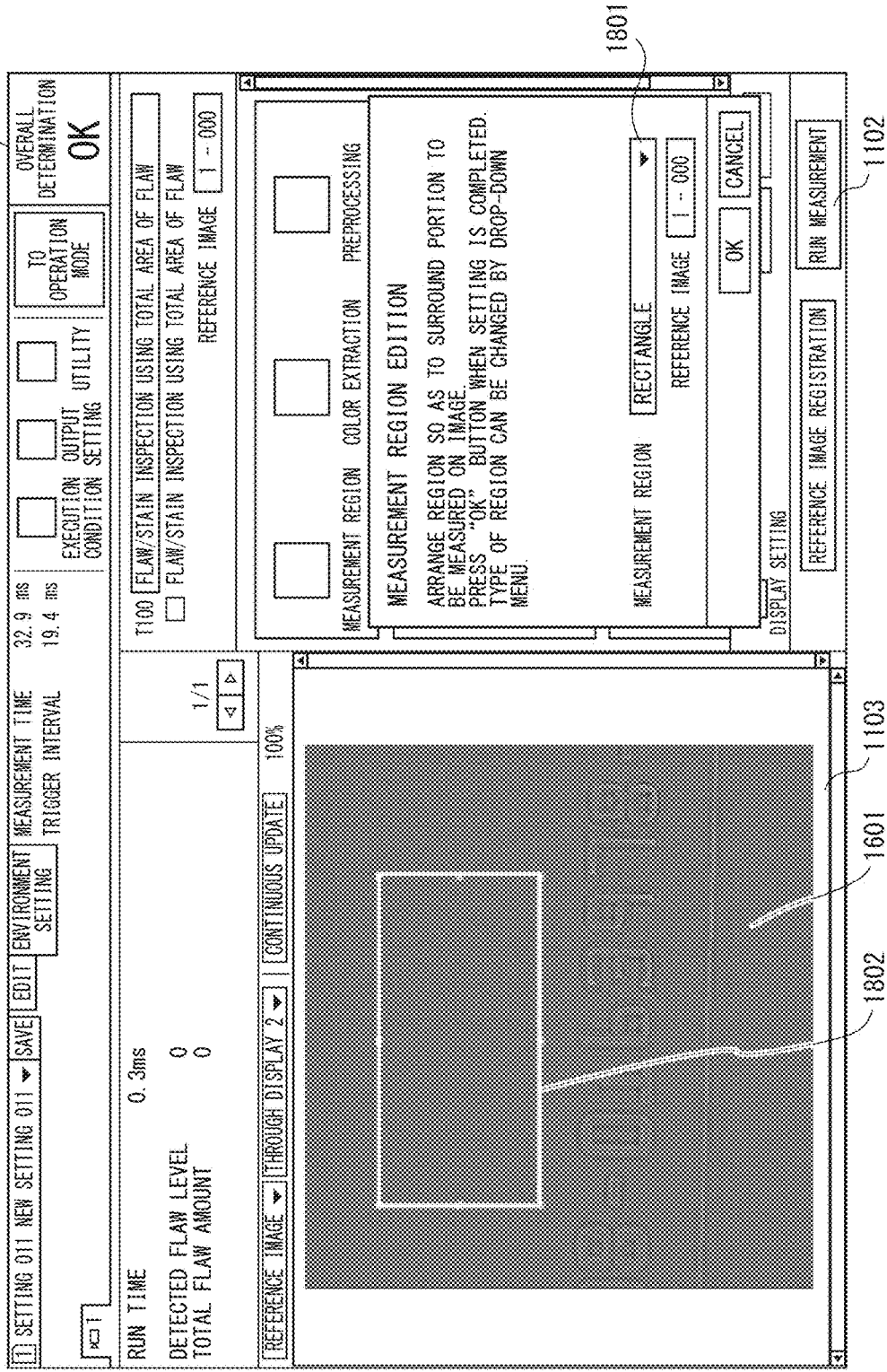
FIG. 18 is a view showing one example of the user interface.

FIG. 18 shows a measurement region setting UI 1800. The measurement region setting UI 1800 is provided with a frame 1802 for showing a measurement region. A shape of the frame 1802 is changeable, and for example, any shape out of a plurality of shapes is selected by a pull-down menu 1801 for selecting the shape. The UI managing part 814 renders the frame 1802 having the shape selected by the pull-down menu 1801 to the display region 1103. The UI managing part 814 changes a position and a size of the frame 1802 in accordance with designation from the input part 6.

Figure 19:
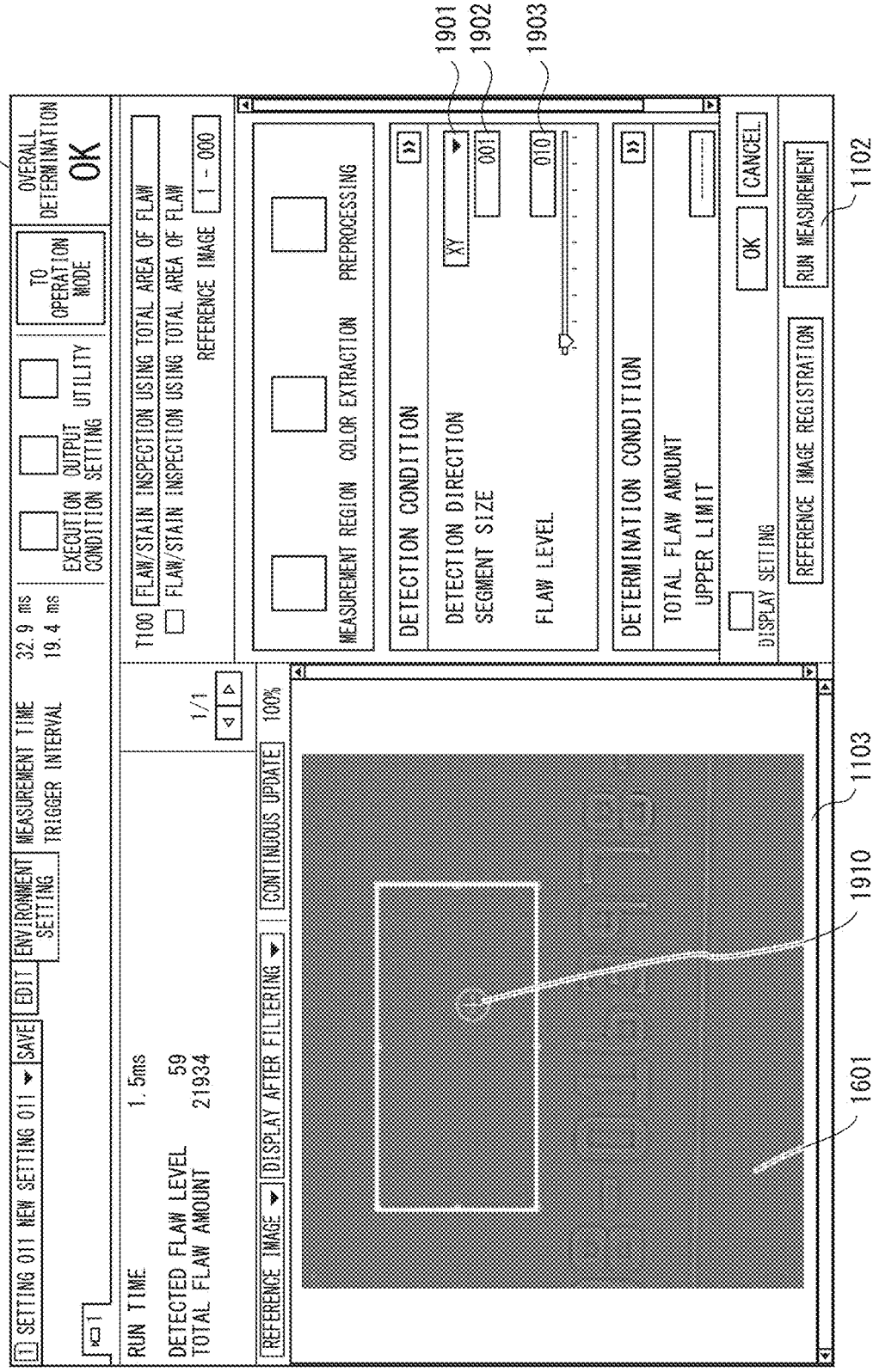
FIG. 19 is a view showing one example of the user interface.

FIG. 19 shows a setting UI 1900 for setting flaw detecting conditions. The setting UI 1900 is provided with a pull-down menu 1901 for selecting a flaw detecting direction, a box 1902 for designating a flaw segment size, and a slider 1903 for designating a flaw level. When the flaw inspection part 831 detects a flaw based on the flaw detecting conditions set by the setting UI 1900, the UI managing part 814 may display a flaw detection mark 1910 at a position of the flaw. This allows the user to judge whether or not the flaw detection conditions are suitable.

<Inspection Mode>

Figure 20:
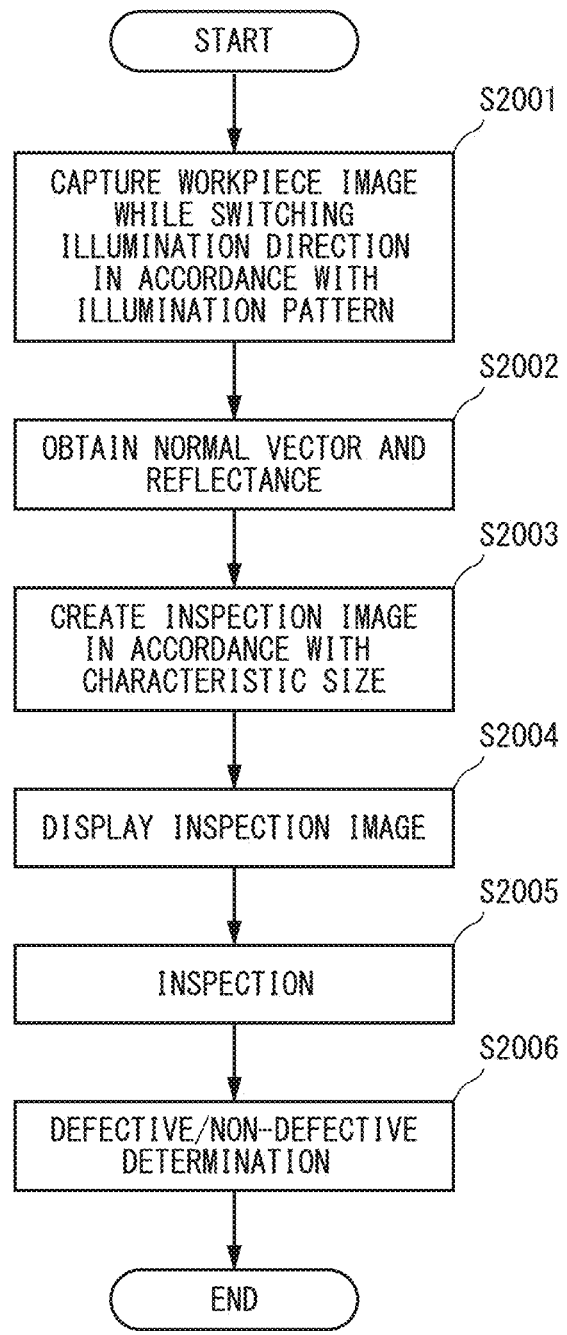
FIG. 20 is a flowchart showing an inspection mode.

FIG. 20 is a flowchart showing the inspection mode. When the start of the inspection mode is designated through the input part 6, the processor 810 switches the operation mode to the inspection mode.

In S2001, the processor 810 captures and acquires an image of the workpiece 2 while switching the illumination direction in accordance with the set illumination pattern. Specifically, the illumination control part 812 specifies the illumination pattern with reference to the setting data held in the storage device 820, and transmits a command for designating the illumination pattern to the illumination controller 802. The imaging control part 813 specifies control parameters (shutter speed, sensitivity, and the like) concerning the camera 4 with reference to the setting data held in the storage device 820, and transmits a command for designating the control parameters to the camera 4. The photometric processing part 811 transmits a trigger signal for designating the start of illumination to the illumination controller 802, and in conjunction with this, the photometric processing part 811 transmits a trigger signal for designating the start of imaging to the camera 4. The illumination controller 802 switches the illumination direction in synchronization with the trigger signal. For example, in accordance with the illumination pattern designated by the command, the illumination controller 802 lights the corresponding light-emitting elements sequentially one by one with respect to the four illumination directions. The illumination controller 802 may hold the corresponding relation between the command and the illumination pattern in a memory or the like. Only one trigger signal may be issued at the start of illumination, or the trigger signal may be issued at switching timing. The camera 4 captures an image of the workpiece 2 in accordance with the control parameters, and transfers the luminance image to the image processing apparatus 5. In such a manner, for example, one luminance image is generated for one illumination direction.

In S2002, the processor 810 obtains the normal vector n and the reflectance ρ from the plurality of luminance images. As described above, the photometric processing part 811 applies Expression 1 to pixel values of the plurality of luminance images, to obtain the normal vector n and the reflectance ρ.

In S2003, the processor 810 generates an inspection image in accordance with the set characteristic size. As described above, the photometric processing part 811 decides the weight W corresponding to the characteristic size from a weight table or the like, and performs the accumulation computing by using Expression 2, to generate an inspection image (inclination image). As thus described, the photometric processing part 811 may generate an inclination image having a pixel value based on the normal vector n of the surface of the workpiece 2 from the plurality of luminance images. When a plurality of characteristic sizes with respectively different values are set, the photometric processing part 811 may generate an inspection image with respect to each of the plurality of characteristic sizes. Further, the photometric processing part 811 may generate a reflectance image or a texture image by the foregoing technique. For example, the photometric processing part 811 may calculate the reflectance ρ of the surface of the workpiece 2 along with the normal vector n of the surface of the workpiece 2 from the plurality of luminance images, to generate a reflectance image having a pixel value based on the reflectance p. Here, an image to be inspected is generated, and generation of an image not to be inspected may be omitted.

In S2004, the processor 810 displays the inspection image on the display part 7. The UI managing part 814 may simultaneously or selectively display on the display part 7 the luminance image, the inclination image, and the reflectance image along with the inspection image. When the images are selectively displayed, the UI managing part 814 may, for example, display the four luminance images by sequentially switching in accordance with switching designation from the input part 6. For example, out of the input part 6, a specific key provided in the console may be allocated as an image switching button.

In S2005, the processor 810 designates the image processing part 830 to execute the inspection. When the inspection is designated, the image processing part 830 activates a previously set inspection tool, to execute the inspection on the inspection image. For example, the flaw inspection part 831 discriminates a flaw level in accordance with the set measurement region and detection conditions, and transmits a result of the inspection (flaw level) to the determination part 840. Note that the flaw inspection part 831 may execute a pattern search by using the foregoing reference image and set an inspection region, to execute the inspection in the inspection region. Further, the OCR part 832 performs character recognition processing on the inspection image in accordance with a previously set character recognition setting, and transmits a result of the character recognition to the determination part 840. The OCR part 832 may also execute a pattern search by using the foregoing reference image and set an inspection region (character recognition region), to execute the inspection in the inspection region.

In S2006, the determination part 840 of the processor 810 compares the inspection result and a determination threshold, to determine whether or not the workpiece 2 is a non-defective product. For example, in a case where a setting has been performed so as to execute both the flaw inspection and the OCR, the determination part 840 determines the workpiece 2 as a non-defective product when both of the result of the inspection by the flaw inspection part 831 and the result of the character recognition by the OCR part 832 are at passing levels.

<Image Saving Setting>

Figure 21:
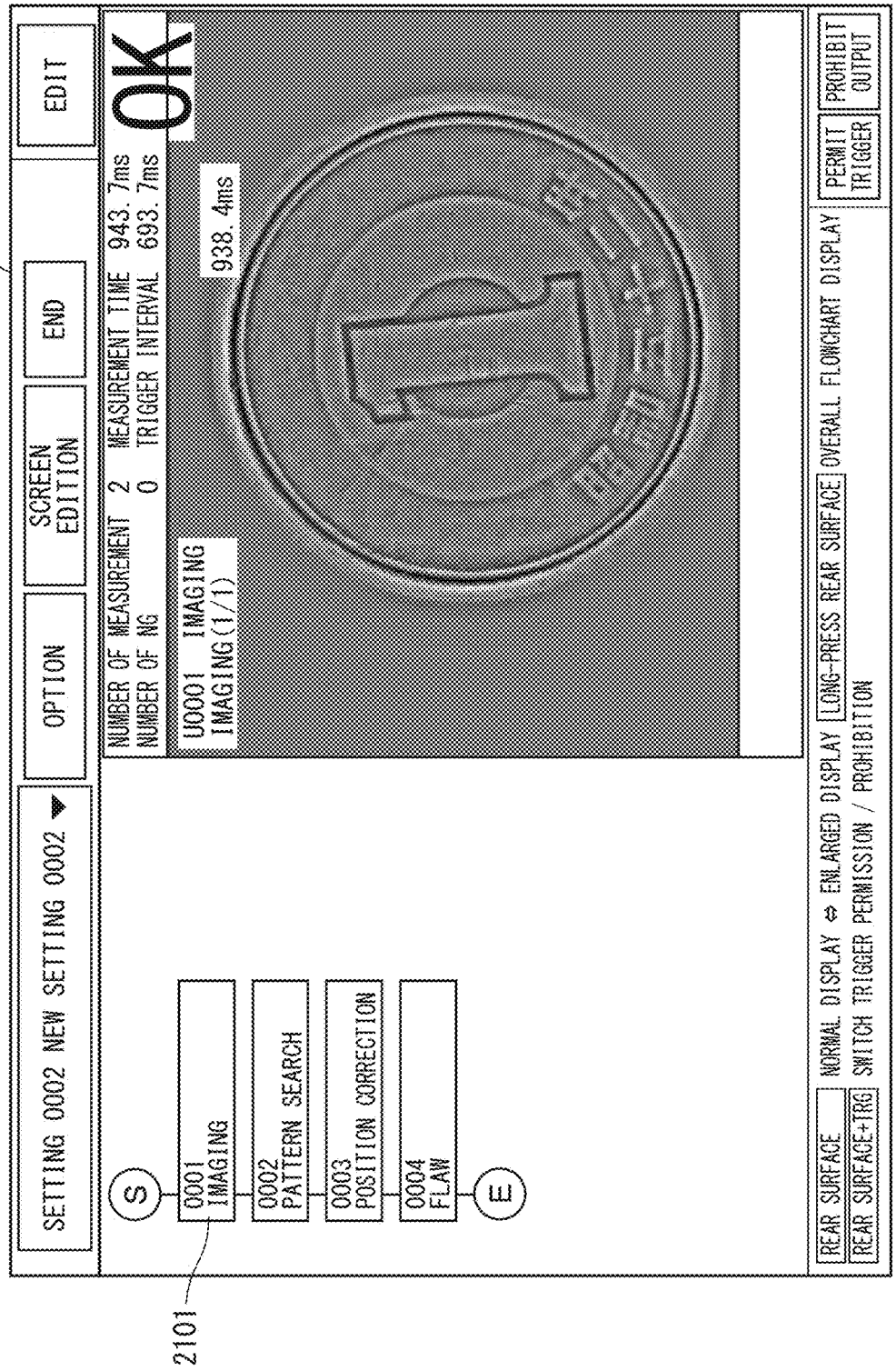
FIG. 21 is a view showing one example of the user interface.

FIG. 21 shows one example of a UI 2100 for setting an inspection flow. The UI managing part 814 displays the UI 2100 on the display part 7, and sets a plurality of steps to be performed from the start to the end of the inspection flow in accordance with designation inputted from the input part 6. In this example, an imaging step, a pattern search step, a position correcting step and a flaw inspecting step are added to the inspection flow. For example, when the end of the inspection flow is designated through the input part 6, the UI managing part 814 may perform such a setting as to store an inspection history at the end. The inspection history is an inspection result, an image used in the inspection, and the like.

At the time of adding each step, the UI managing part 814 may accept selection of an image to be used in each step through the input part 6. For example, through the input part 6, the user may designate four luminance images with four different illumination directions, an inclination image, a reflectance image, or the like as an acquirement target for the imaging step. The user may designate any of luminance images (all-directional illumination image, etc.) as a search target for the pattern search step. The user may designate an inspection image generated from the inclination image as an inspection target for the flaw inspecting step. In the present embodiment, a plurality of shape images and a reflection image generated from the plurality of luminance images captured in the imaging step can be outputted in the later-stage inspection step, whereby the user can apply a plurality of inspection images generated from the common imaging step to a variety of inspections corresponding to characteristics of each image.

Figure 22:
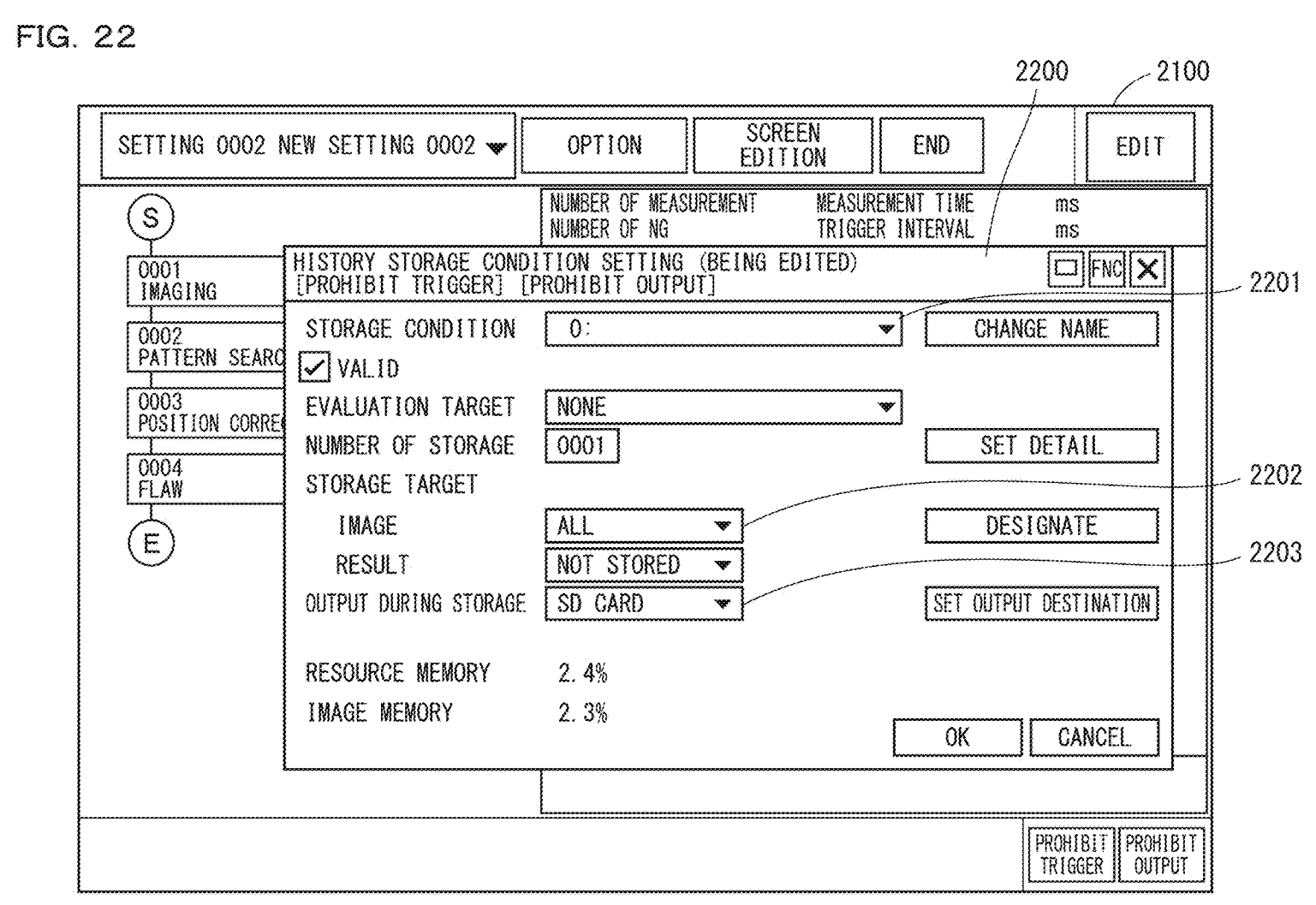

FIG. 22 shows one example of a UI 2200 for setting a condition for storing histories. A setting part 2201 for setting identification information for identifying the storage condition is a pull-down menu for selecting identification information to be set from a plurality of pieces of identification information. In this example, in the setting part 2201, a storage condition for identification information of "0:" is selected. Examples of the storage condition includes a condition that images are stored only when an inspection result shows that the workpiece is not a non-defective product, and a condition that images are constantly stored for each workpiece without depending on the inspection result. Here, the processor 810 activates the condition setting part 819 when detecting that a detail setting button or the like is pressed. The condition setting part 819 may, for example, set one of a mode for constantly saving or outputting an image, and a mode for saving or outputting an image when the determination part 840 determines that an inspection target is not a non-defective product. An image selection part 2202 selects an image that is saved when the storage condition is satisfied. Here, "all" or "designate" can be selected by the image selection part 2202. A saving destination selection part 2203 is a pull-down menu for selecting an image saving destination (e.g., a portable medium such as an internal memory or a memory card, or network storage such as an FTP server).

Figure 23:
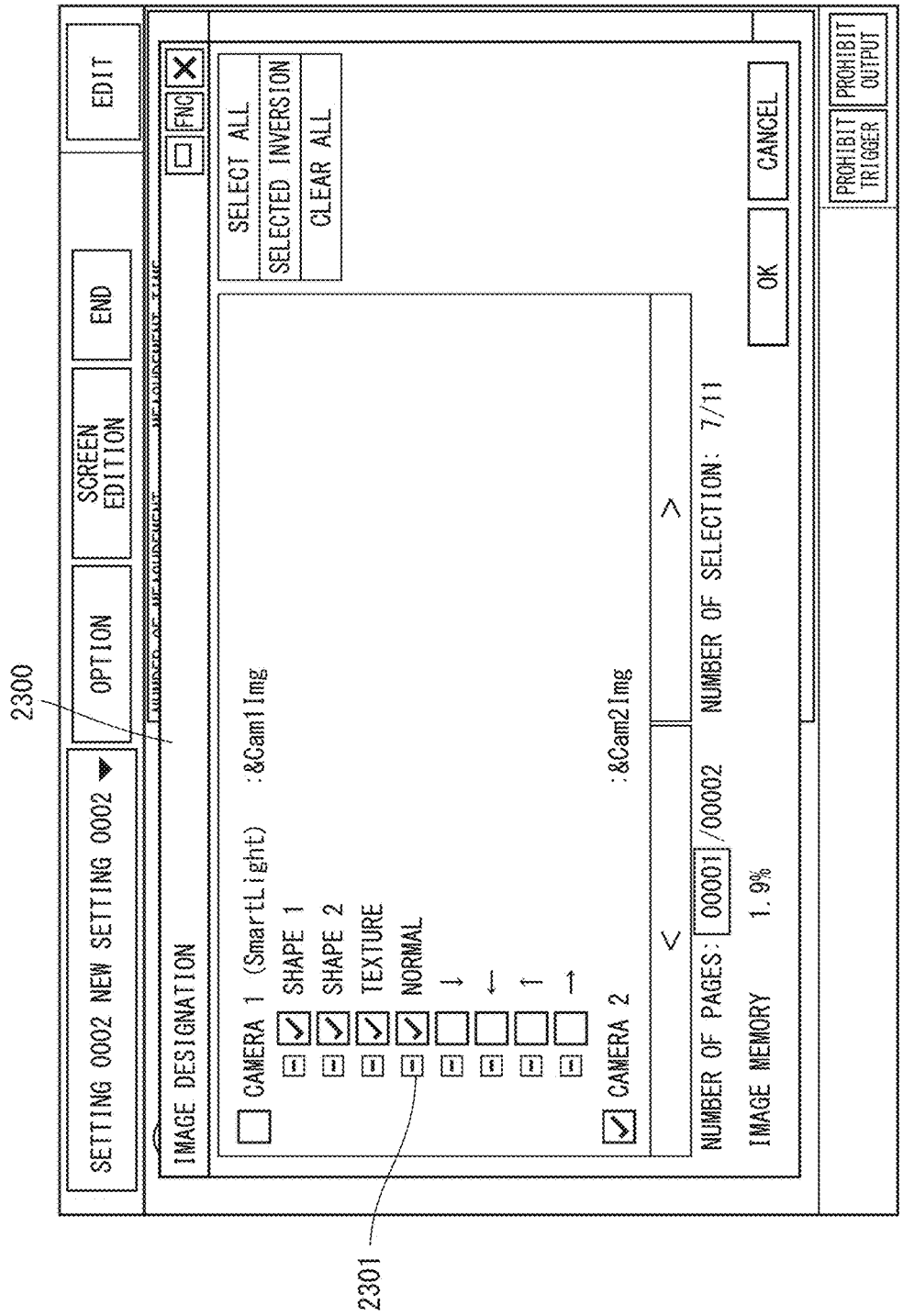
FIG. 23 is a view showing one example of the user interface.

FIG. 23 shows one example of a UI 2300 that the UI managing part 814 displays on the display part 7 when "designate" is selected in the image selection part 2202. In this example, there is provided a check box 2301 for selecting an image to be actually saved out of all types of images handled in the inspection flow. "Shape 1" and "shape 2" are inspection images (inclination images) with different characteristic sizes. "Texture" is a reflectance image. "Normal" is an image acquired by all-directional illumination. Each of four arrows indicates an illumination direction. That is, four luminance images with different illumination directions are discriminated by the arrow marks.

An image whose check box is checked is set as an image to be saved.

Incidentally, the processor 810 may be provided with a judgment section for judging whether or not a condition for saving or outputting an image is satisfied after the determination part 840 completes the determination. That is, in the end part of the inspection flow, the processor 810 may judge whether or not the storage condition or the output condition set by the condition setting part 819 is satisfied.

Figure 24:
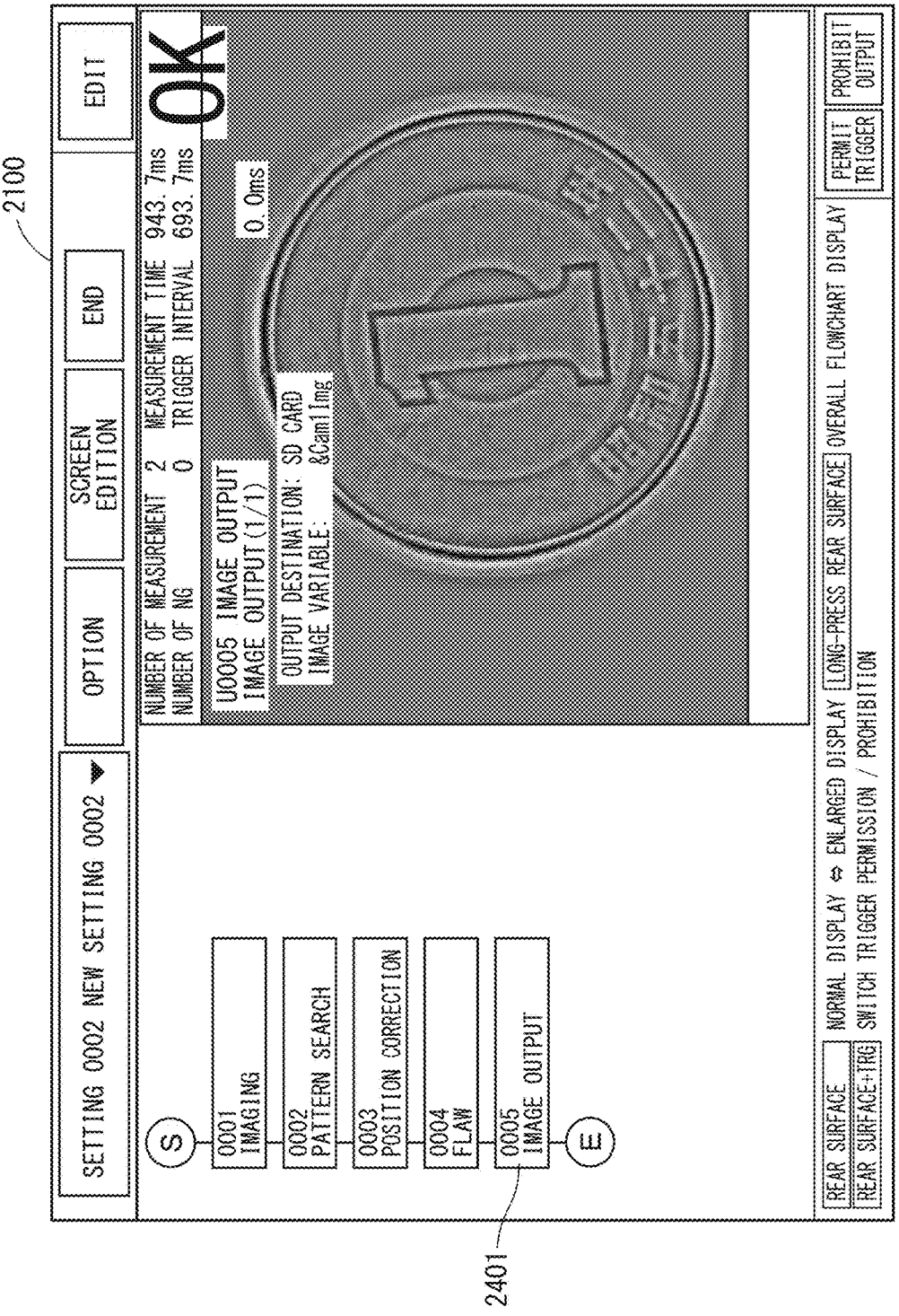
FIG. 24 is a view showing one example of the user interface.

FIG. 24 shows an example of adding an image outputting step 2401 to the inspection flow. In the foregoing example, the setting has been performed so as to output an image at the end of the inspection flow, but in this example, the UI managing part 814 sets the image outputting step 2401 at an arbitrary position of the inspection flow in accordance with the user's designation inputted from the input part 6. In such a manner, the processor 810 may judge whether or not the condition for saving or outputting an image is satisfied in the image outputting step 2401 located before the determination part 840 completes the determination. The storage setting and the like related to the image outputting step 2401 may be similar to those described using FIGS. 21 to 23, or may be different.

Figure 25:
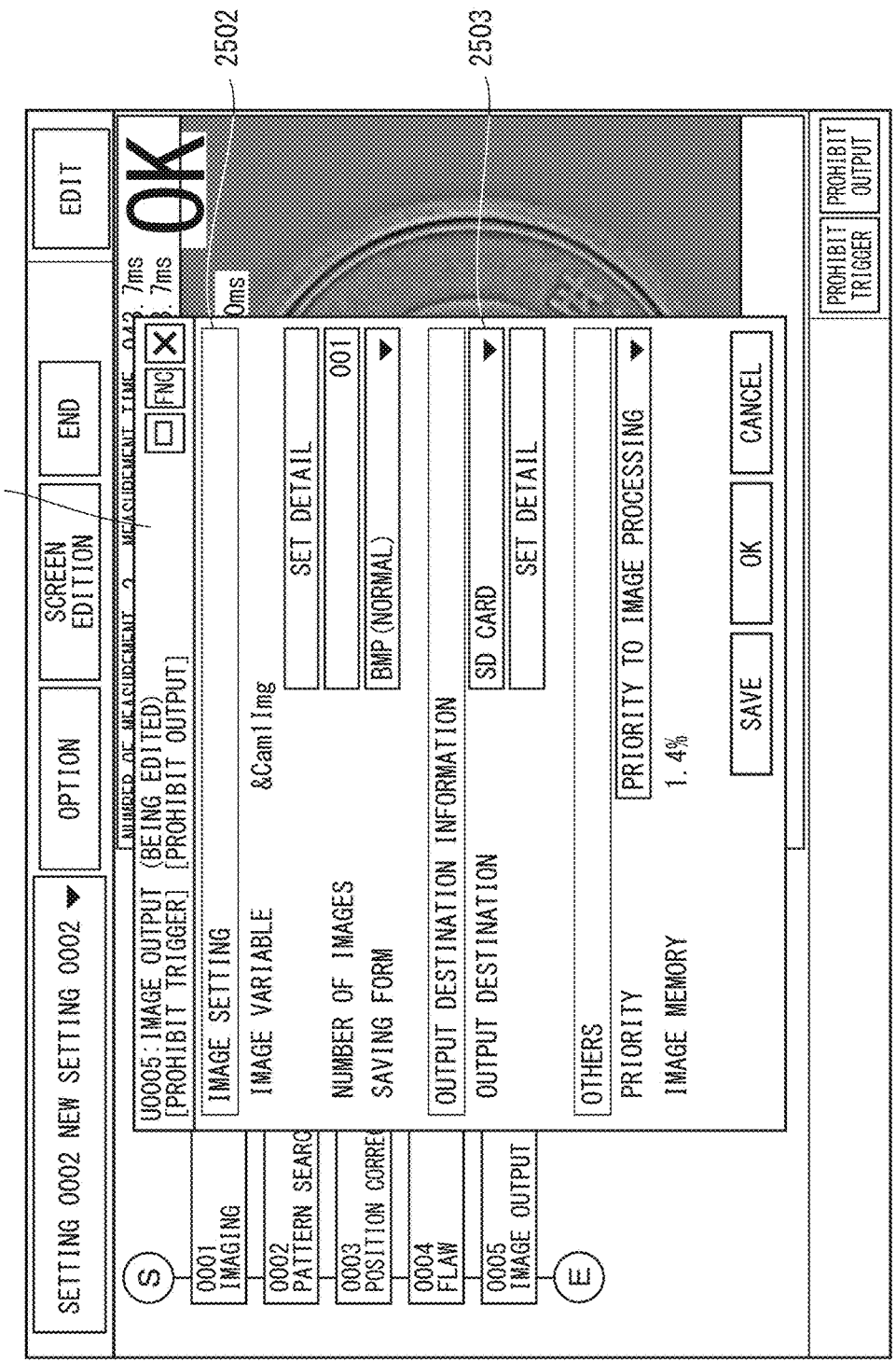
FIG. 25 is a view showing one example of the user interface.

FIG. 25 shows a different example of a UI related to the storage setting (output setting). In a state where the image outputting step 2401 has been selected by the input part 6, when designation to start a setting is further inputted by the input part 6, the UI managing part 814 displays a UI 2501. An image variable 2502 functions as an image selection part for selecting an image to be outputted, and in this example, an image to be outputted is designated by the image variable that is added to each step in the inspection flow. That is, the image to be outputted can be selected for each step. In the UI 2501, the number of outputted images, an image form, and the like may be set. An output destination selection part 2503 is a pull-down menu for selecting an image outputting destination (e.g., a portable storage medium such as an internal memory or a memory card, or network storage such as an FTP server).

Figure 26:
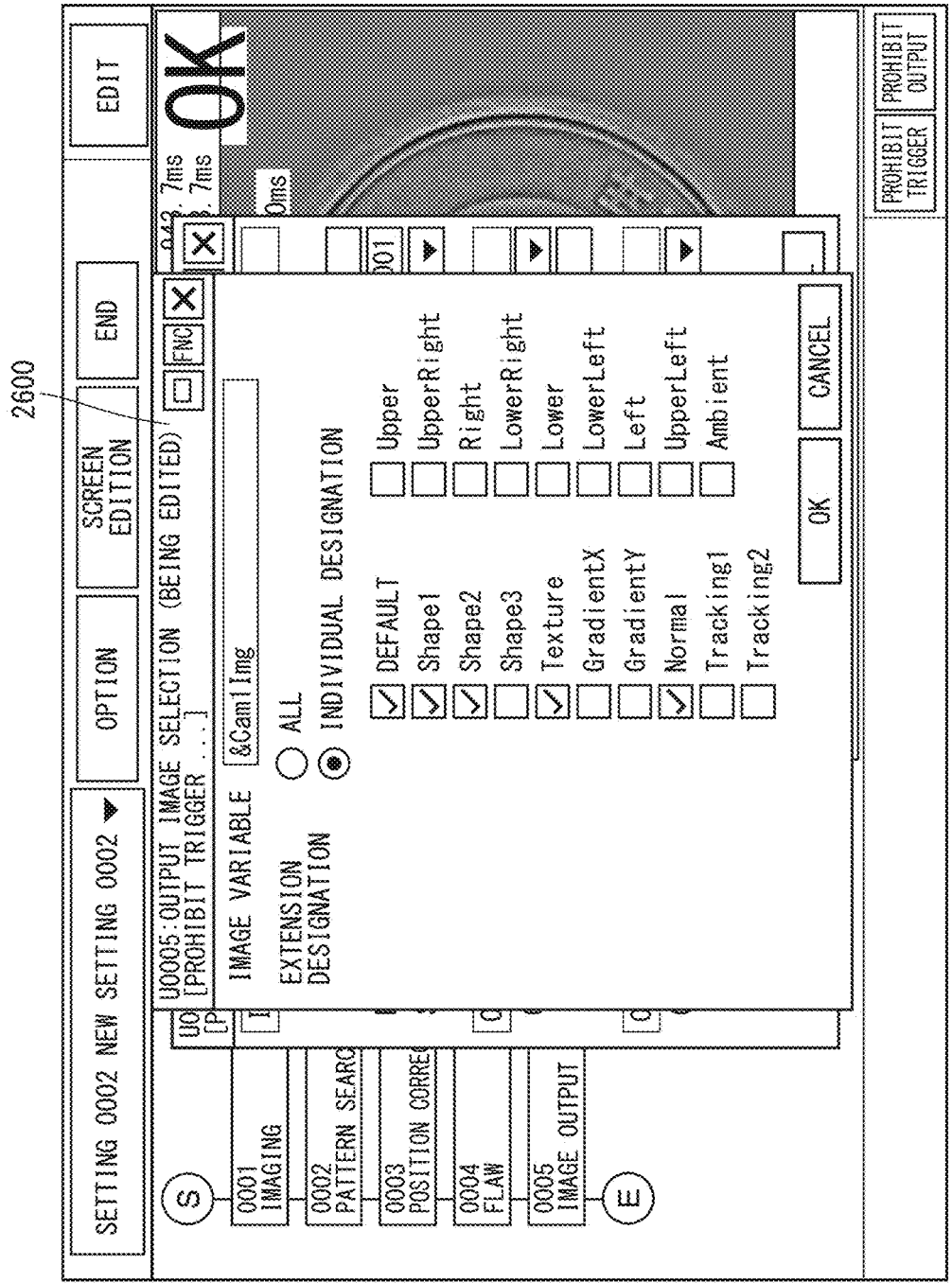
FIG. 26 is a view showing one example of the user interface.

FIG. 26 is one example of a UI 2600 for selecting an image. When a detail setting button is pressed down in the UI 2501, the UI managing part 814 displays a UI 2600. The UI 2600 is provided with a radio button for selecting whether to save all images or to individually designate the images, check boxes for individually selecting the images, and the like. In this example, since the individual setting is selected by the radio button, check boxes are enabled, and several images are selected by the check boxes. In such a manner, an image to be saved or outputted may be selected out of a plurality of luminance images, an inspection image, an all-directional illumination image, and a synthesized luminance image obtained by synthesizing the plurality of luminance images. Further, the UI 2600 may be configured so as to select an image, which is to be saved or outputted, out of a plurality of inspection images with respectively different characteristic sizes. Moreover, the UI 2600 may be configured such that an image to be saved or outputted can be selected out of a plurality of luminance images, an inspection image, and a reflectance image whose pixel value is a reflectance of the surface of the inspection target.

<Display of Image in Parameter Adjustment>

Adjusting the control parameter while checking the luminance image and the inspection image as described above allows the user to easily decide an appropriate control parameter. Here, a specific example of a UI concerning parameter adjustment will be shown.

Figure 27:
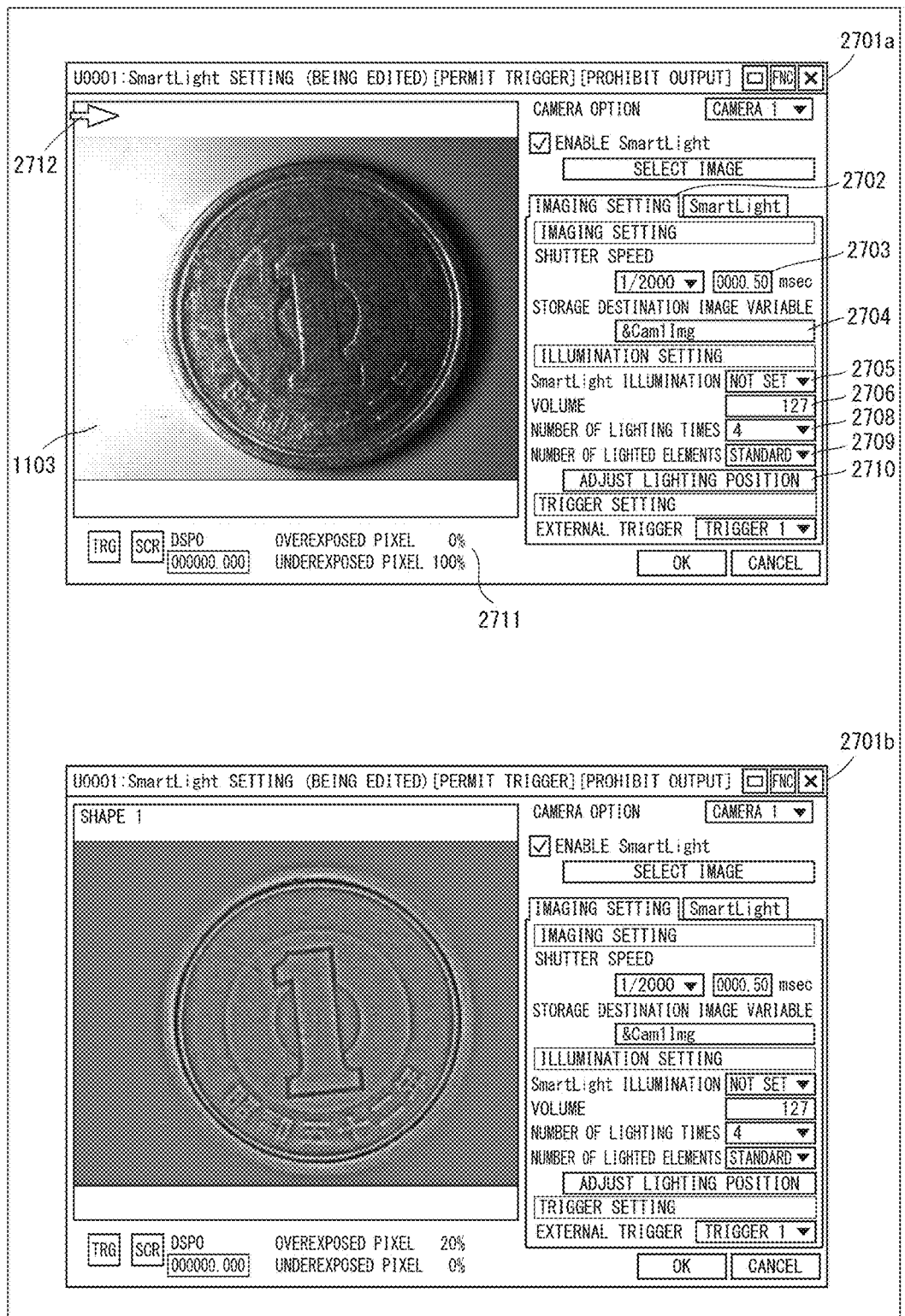
FIG. 27 is a view showing one example of the user interface.

FIG. 27 shows one example of UIs 2701a, 2701b that the UI managing part 814 displays on the display part 7 at the time of adjusting control parameters. The UI 2701a and the UI 2701b are different in an image displayed in the display region 1103. An imaging setting tab 2702 is a UI for setting control parameters such as an imaging condition of the camera 4 and an illumination condition of the illumination apparatus 3. A shutter speed setting part 2703 is a pull-down menu for designating a shutter speed of the camera 4, and one shutter speed is selectable from a list of a plurality of shutter speeds. An image variable setting part 2704 is a text box where a variable for storing an image acquired by the camera 4 is inputted. An illumination pattern setting part 2705 is a pull-down menu for designating one illumination pattern out of a plurality of illumination patterns. The illumination pattern is, for example, a pattern which determines the lighting order of an element out of annularly arrayed sixteen elements. A light amount setting part 2706 is a text box for setting a light amount level of the illumination apparatus 3. A number-of-lighting-times setting part 2708 is a pull-down menu for selecting the number of times the illumination apparatus 3 is lighted on one workpiece. A standard number of lighting times is four, but another number of lighting times such as eight is also settable. When the number of times is set to eight, the number of illumination directions is eight, and the number of luminance images also is eight. Increasing the number of illumination directions and the number of luminance images facilitates detection of a finer flaw and improves inspection accuracy even in a workpiece where halation is apt to occur. A number-of-lighted-elements setting part 2709 is a pull-down menu for setting the number of light-emitting elements that are lighted in one lighting timing. For example, when illumination light is illuminated from four illumination directions, the number of light-emitting elements lighted per one illumination direction can be changed from one to two, three and four. A lighting position adjusting part 2710 is a UI for setting which light source group is firstly lighted in each illumination pattern. Actual arrangement of the illumination apparatus 3 may not match with arrangement assumed by the inspection apparatus. For example, even in a case where lighting is performed on the workpiece 2 from the right direction, when the illumination apparatus 3 is attached as rotated 90 degrees from a predetermined position, an actual illumination direction is the upward direction or the downward direction. When the illumination pattern is the order of right, bottom, left and top, by changing the order to the order of bottom, left, top and right, the actual arrangement of the illumination apparatus 3 comes to match with the arrangement assumed by the inspection apparatus. When the lighting position adjusting part 2710 is activated, the UI managing part 814 may display a user interface for designating a light source (light-emitting element) to be lighted. An inspection tool setting part may accept designation of the light source to be lighted through this UI. According to FIG. 27, the display control part 851 superimposes and displays, on each luminance image, an arrow 2712 that indicates an illumination direction assumed concerning the luminance image. This allows the user to determine whether or not the actual illumination direction matches with the computed illumination direction.

The display control part 851 of the UI managing part 814 may obtain pixels (overexposed pixels and underexposed pixels) whose pixel values are saturated in an image being displayed in the display region 1103, and emphasize (e.g., display in red, blink, and the like) these pixels. In order to clarify overexposed pixels and underexposed pixels, the display control part 851 may color the overexposed pixels and the underexposed pixels respectively different colors (e.g., red and blue). Further, overexposure and underexposure cannot be seen by just looking at the inspection image. This is because the inspection image is not intended to show luminance, but to show a normal vector (inclination) or the like. Therefore, the display control part 851 may obtain positions (coordinates) of the overexposed pixels and the underexposed pixels in the luminance image, and out of pixels constituting the inspection image, the display control part 851 may emphasizes pixels at positions matching with the positions of the overexposed pixels and the underexposed pixels in the luminance image. This allows the user to recognize occurrence of the overexposed pixels and the underexposed pixels by looking at the inspection image. Naturally, emphasis may be performed only in the luminance image where the overexposed pixels and the underexposed pixels actually occur. Since the user can switch and display the inspection image and the luminance image as described above, the overexposed pixels and the underexposed pixels can be checked in the luminance image. The display control part 851 may obtain the positions and number of saturated pixels from pixels constituting a synthesized luminance image, to emphasize the saturated pixels in the synthesized luminance image or emphasize the saturated pixels in the inspection image.

The display control part 851 may display a rate of the overexposed pixels and a rate of the underexposed pixels in a notification part 2711 together with or in place of emphasis of the overexposed pixels and the underexposed pixels. The rate may be a ratio of saturated pixels to non-saturated pixels, or a ratio of saturated pixels to all pixels constituting the image. The display control part 851 may count the number of overexposed pixels and the number of underexposed pixels in each of a plurality of luminance images, calculate a rate of the overexposed pixels from the maximum value of the number of overexposed pixels, and calculate a rate of the underexposed pixels from the maximum value of the number of underexposed pixels, to display these ratios in the notification part 2711. In this case, irrespective of the type of the image displayed in the display region 1103, the rate of the overexposed pixels and the rate of the underexposed pixels are displayed in the notification part 2711.

By emphasizing overexposed pixels and underexposed pixels or displaying a rate of the overexposed pixels and a rate of the underexposed pixels as thus described, it is possible to adjust a shutter speed, a light amount, a diaphragm of a lens, and the like while checking an image displayed in the display region 1103 until the overexposed pixels and the underexposed pixels become nonexistent.

When designation to switch a display image is inputted through the input part 6, the display control part 851 may display a previously set image switched from the currently displayed image. For example, every time switching designation is inputted, the display control part 851 may sequentially display, on the display part 7, four luminance images with respectively different illumination directions, and an inclination image, a reflectance image, a surface shape image, a texture image, or a synthesized luminance image, which is generated from the luminance images. Further, the number of inspection images may be plural. For example, every time switching designation is inputted, the display control part 851 may sequentially display a plurality of inspection images (surface shape images) with respectively different characteristic sizes on the display part 7. According to FIG. 27, a luminance image captured by illuminating illumination light from the left direction is displayed in the UI 2701*a*, and an inspection image is displayed in the UI 2701*b*. When the UI managing part 814 accepts a change in any of the control parameters in the imaging setting tab 2702, the inspection tool setting part 817 sets the changed control parameter in the illumination control part 812 and the imaging control part 813. The illumination control part 812 sets the changed control parameter in the illumination controller 802. The illumination controller 802 sets the light source group 801 in accordance with the changed control parameter. The imaging control part 813 controls the camera 4 in accordance with the changed control parameter to acquire a luminance image. The photometric processing part 811 receives the newly acquired luminance image and regenerates (updates) the inclination image, the reflectance image, the inspection image, or the like. When being notified of updating of the image from the photometric processing part 811, the display control part 851 reads the updated image from the storage device 820 and displays the updated image in the display region 1103.

Displaying the luminance image and the inspection image while switching them as thus described allows the user to find an appropriate control parameter. Further, updating an image in real time upon a change in control parameter further allows the user to find an appropriate control parameter.

Figure 28:
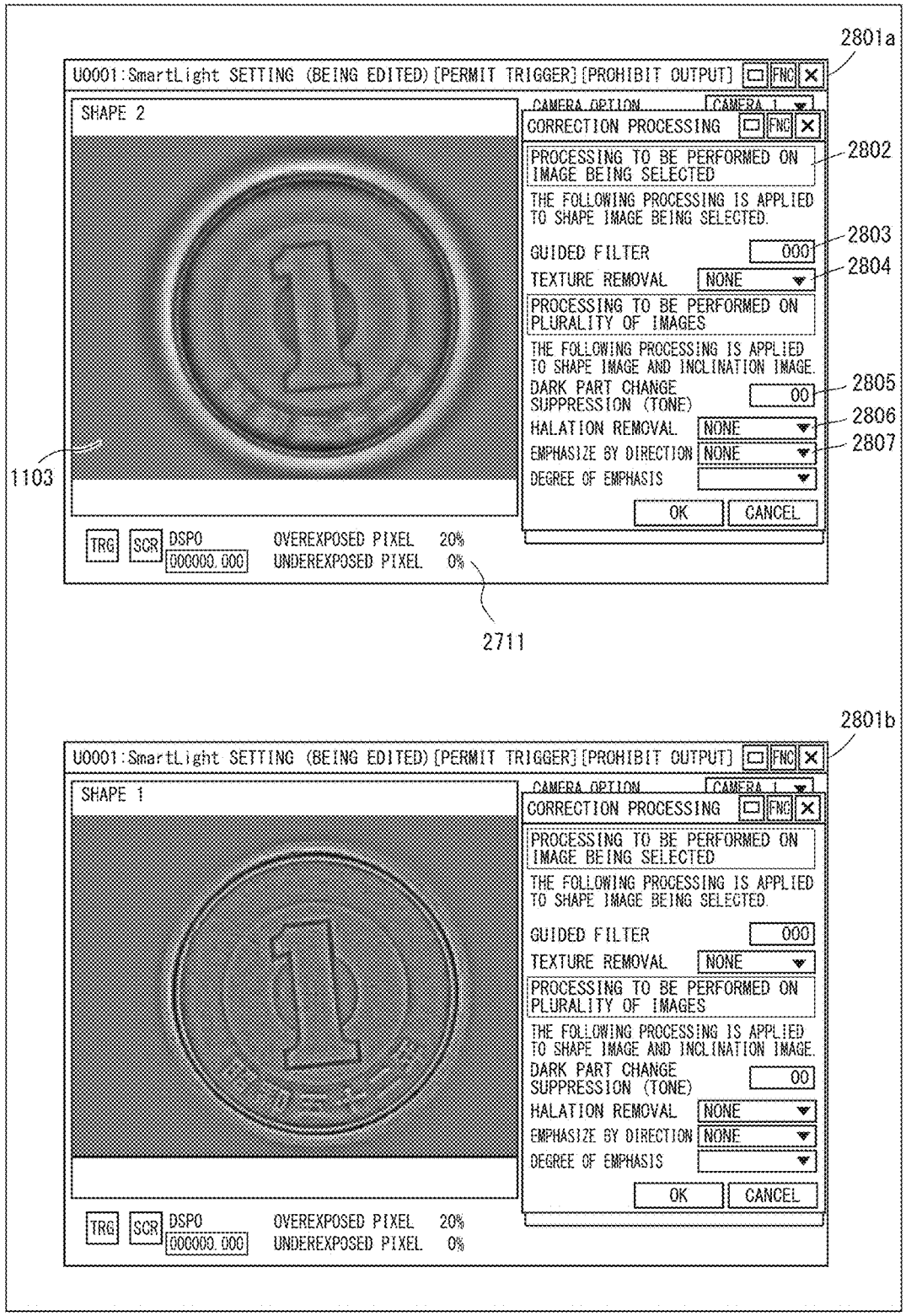
FIG. 28 is a view showing one example of the user interface.

FIG. 28 shows one example of UIs 2801a, 2801b that the UI managing part 814 displays on the display part 7 at the time of adjusting control parameters. The UIs 2801a, 2801b are used for adjusting control parameters related to image correction processing (generation conditions for an inspection image and the like) out of the control parameters. Further, a correction processing setting part 2802 in each of the UIs 2801a, 2801b adjusts an individual setting that is applied only to a displayed image, and a common setting that is commonly applied to a plurality of images. As the individual setting, for example, a guided filter setting part 2803 and a texture removal setting part 2804 are provided. A guided filter is a filter for smoothing an image. Here, a smoothing level can be set. Texture removal means removing an influence of a design and printing on the surface of the workpiece 2. As the common setting, a dark-part change suppression setting part 2805, a halation removal setting part 2806, and an emphasis-by-direction setting part 2807 are provided. Dark-part change suppression is processing for suppressing an influence of noise in a dark part of an image. Halation removal is processing for removing halation in a luminance image to reduce the influence of halation on an inclination image and a surface shape image. Emphasis by direction is processing for emphasizing unevenness in a designated direction out of the x-direction (vertical direction in the inspection image) and the y-direction (horizontal direction in the inspection image), and decreasing unevenness in a non-designated direction.

Figure 29:
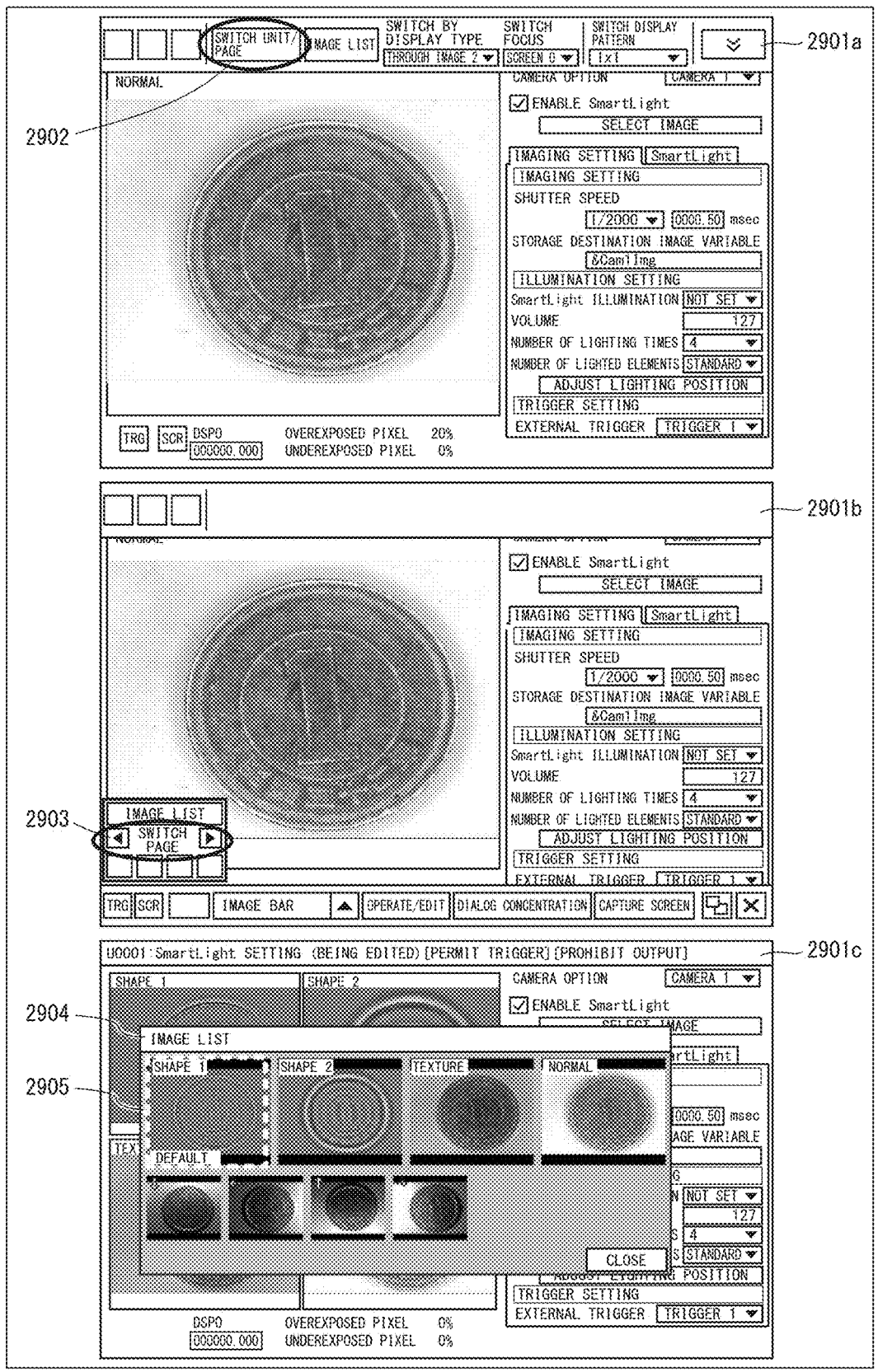
FIG. 29 is a view showing one example of the user interface.
Figure 30:
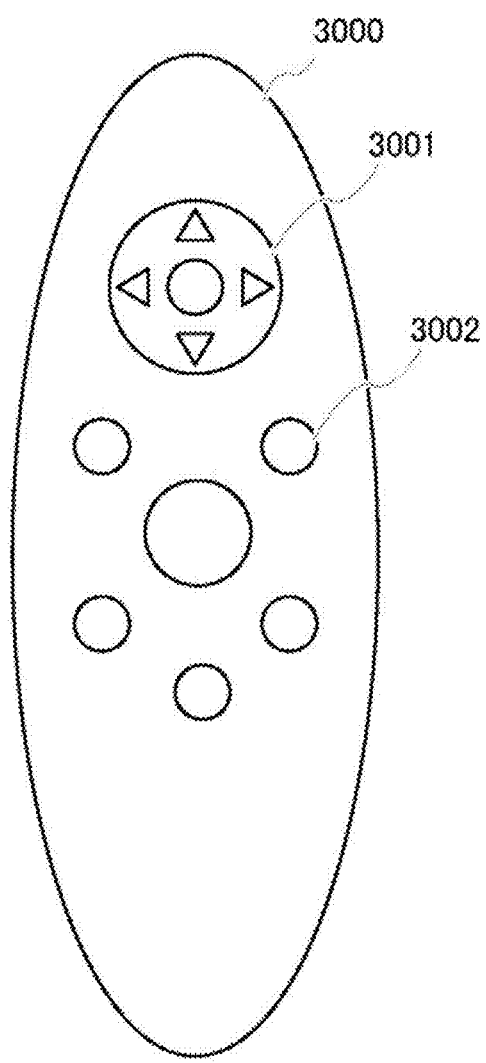
FIG. 30 is a view showing one example of the user interface.

FIG. 29 shows one example of the UIs 2901a, 2901b, 2901c for inputting image switching designation. FIG. 30 shows one example of a console 3000 which is part of the input part 6. The UI 2901a is provided with a page switching part 2902 operated by the console 3000. By operating a vertical/horizontal key 3001 of the console 3000, a page switching part 2902 is made active. When the vertical/horizontal key 3001 is operated in this state, the display control part 851 determines that image switching designation has been inputted.

The UI 2901b is a UI in the case of the input part 6 being mounted by means of a touch panel. When operation of an image switching button 2903 is detected, the display control part 851 determines that image switching designation has been inputted. It is to be noted that the image switching button 2903 is provided with a button for switching an image in a forward direction of the order of a plurality of images, and a button for switching an image in a reverse direction thereof. Accordingly, even when a plurality of images are display targets, an intended image can be rapidly displayed.

The UI 2901c has an image list 2904 and an image selection frame 2905. When display designation of the image list 2904 is inputted through the input part 6, the UI managing part 814 creates and displays the image list 2904.

The display control part 851 displays in the display region 1103 an image selected by the image selection frame 2905 that is operated through the input part 6.

Figure 31:
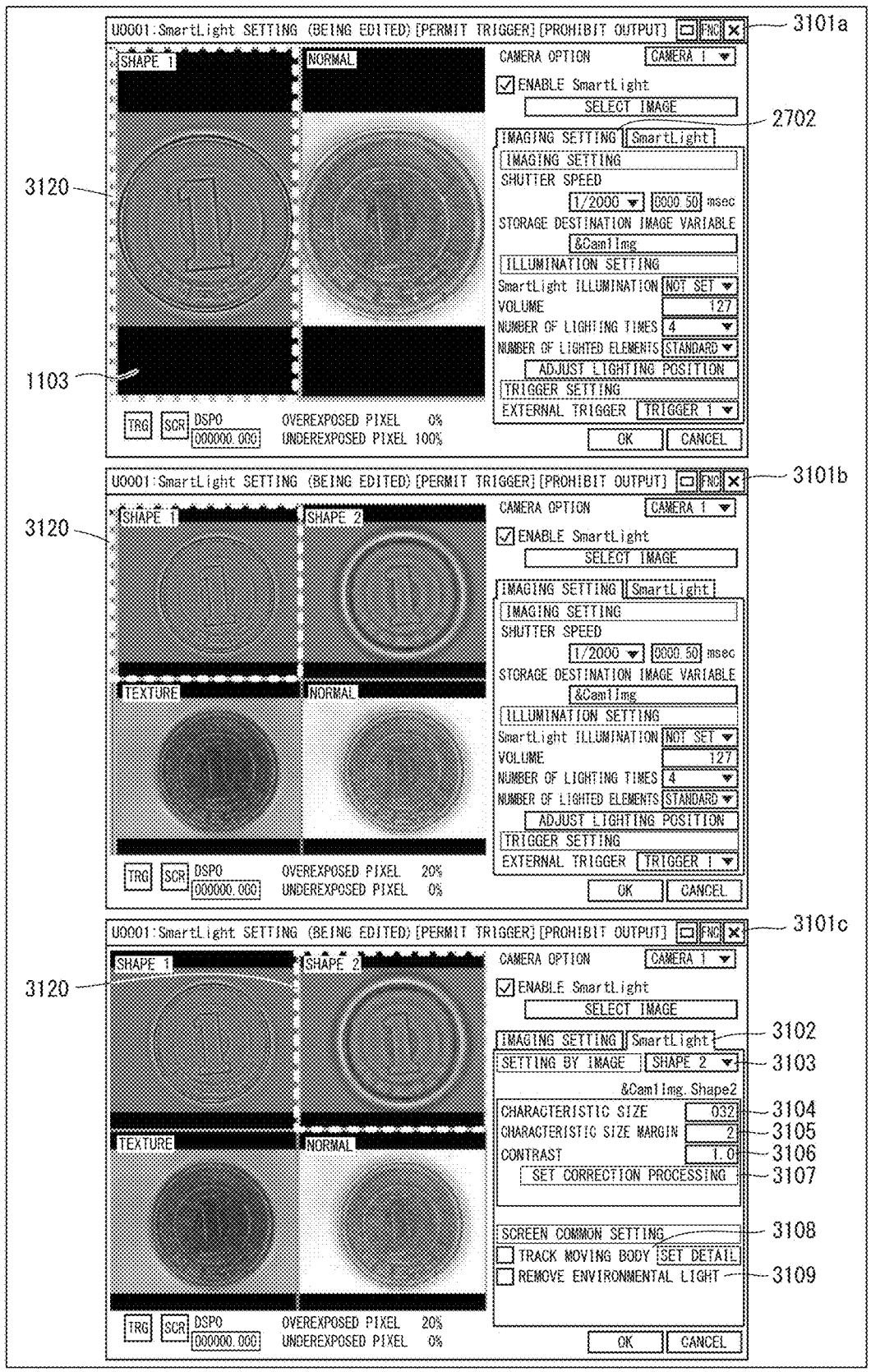
FIG. 31 is a view showing one example of the user interface.

FIG. 31 shows one example of UIs 3101a, 3101b, 3101c that the UI managing part 814 displays on the display part 7 at the time of adjusting control parameters. In UI 3101a, two images such as an inspection image and a luminance image are simultaneously displayed in the display region 1103. In UI 3101b, three inspection images and a luminance image are simultaneously displayed in the display region 1103. When a plurality of images are displayed as thus described, the display control part 851 may display an image selection frame 3120 for selecting an image for which a control parameter is to be adjusted. The display control part 851 changes a position of the image selection frame 3120 in accordance with movement designation inputted from the input part 6. Hence it is possible for the user to select the image for which a control parameter is to be adjusted.

In UI 3101c, a tab 3102 for adjusting control parameters regarding photometric stereo (generation conditions for an inspection image and the like) is enabled. Also in this example, a plurality of inspection images, for which generation conditions are different, are simultaneously displayed in the display region 1103. This facilitates comparing influences on the inspection images exerted due to differences in generation condition. An image selection part 3103 is a pull-down menu for selecting a setting target image. In this example, identification information of each of the four images being displayed in the display region 1103 is displayed in this pull-down menu, and the identification information of one of those images is selected. It is to be noted that the image selection frame 2905 may be superimposed and displayed on the image selected by the image selection part 3103. A characteristic size setting part 3104 is a text box for designating a characteristic size. A margin setting part 3105 is a text box for setting to what extent a margin is made with respect to the characteristic size. When the margin is made small, a shape with a size close to the characteristic size is emphasized. When the margin is made large, a shape with a size away from the characteristic size is emphasized. By changing the margin degree in such a manner, adjustment is made so as to prevent the peak of the characteristic size shown in FIG. 4 from becoming steep and becoming non-steep. A contrast setting part 3106 is a text box for setting contrast of an image. When a correction processing setting button 3107 is operated, the UI managing part 814 calls the correction processing setting part 2802 as shown in FIG. 28. A moving body tracking setting part 3108 is a setting part for setting whether moving body tracking processing is enabled or disabled. The moving body tracking processing is processing for correcting a luminance image so as to match a position of the workpiece 2 within each of a plurality of luminance images when the workpiece 2 is moving. A normal vector and a reflectance are obtained by computing with respect to each pixel. Hence the luminance images are required to be aligned such that the same coordinates therein correspond to the same surface. The moving body tracking processing has an influence on all images generated from the luminance images. Therefore, by checking the effect of the moving body tracking processing while comparing the luminance image and the inspection image, it is possible to appropriately select whether the moving body tracking processing should be enabled or disabled. An environmental light removal setting part 3109 is a setting part for enabling processing for removing light (environmental light) from a fluorescent lamp or the like installed in an inspection environment. When the environmental light removal is enabled, the photometric processing part performs processing for removing the environmental light from the luminance image. The environmental light influences all the luminance images and thus influences the inspection image. Therefore, by checking the effect of the environmental light removal processing while comparing the luminance image and the inspection image, it is possible to appropriately select whether the environmental light removal processing is enabled or disabled.

Figure 32:
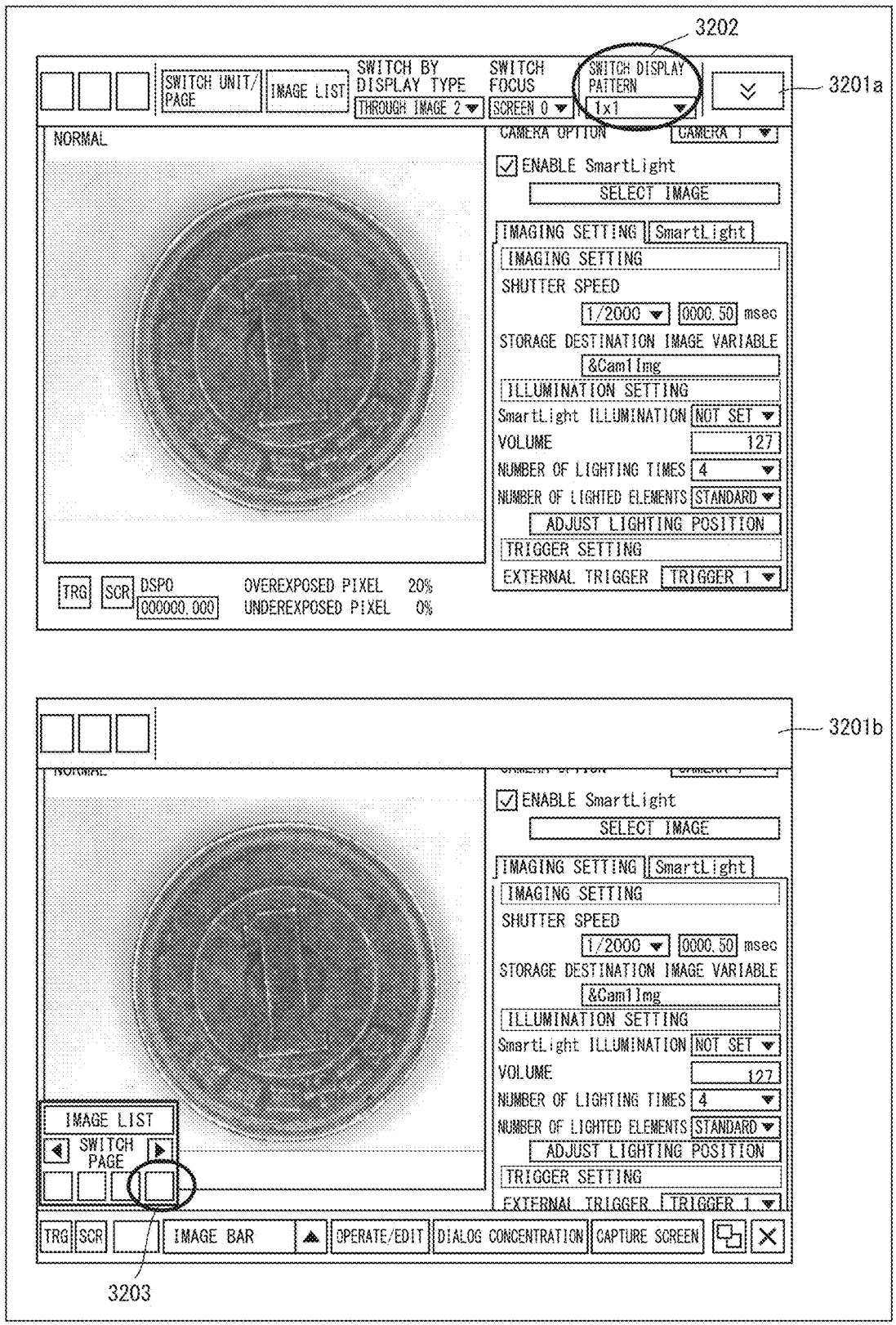
FIG. 32 is a view showing one example of the user interface.

FIG. 32 is a view showing one example of UIs 3201a, 3201b for setting the number of images to be simultaneously displayed. The UI 3201a is a UI to be operated by the console 3000. A display pattern setting part 3202 is a UI for setting how many images are to be displayed in what arrangement in the display region 1103. The UI 3201b is a UI for touch panel. Every time a display pattern switching button 3203 is pressed, the display control part 851 switches a display pattern in the order of: 1×1 (display only one image), 1×2 (display two images horizontally), 2×1 (display two images vertically), 2×2 (display two images each vertically and horizontally), and 1×1.

SUMMARY

According to the present embodiment, the photometric processing part 811 calculates a normal vector of the surface of the workpiece 2 from a plurality of luminance images acquired by the camera 4 in accordance with the photometric stereo method, and performs accumulation computing of a pixel value of a pixel of interest by using a normal vector of a pixel adjacent to the pixel of interest with respect to an inclination image made up of pixel values based on the normal vector calculated from the plurality of luminance images and a reduced image of the inclination image, to generate an inspection image having the pixel value. In particular, according to the present embodiment, there is provided the characteristic size setting part 815 for setting a characteristic size which is a parameter for giving weight to a component of a reduced image that is used in the accumulation computing. As thus described, by introducing the concept of the characteristic size, a parameter can be easily set at the time of generating an inspection image from an image acquired by using the photometric stereo principle.

The characteristic size setting part 815 may set a plurality of characteristic sizes with respectively different values. In this case, the photometric processing part 811 may generate an inspection image with respect to each of the plurality of characteristic sizes set by the characteristic size setting part 815. It is considered that a suitable characteristic size differs according to a type of the inspection tool. Therefore, generating inspection images in accordance with a plurality of characteristic sizes with respectively different values is advantageous in selecting a more suitable image corresponding to the inspection.

The flaw inspection part 831 may execute flaw inspection on a plurality of inspection images generated by using respectively different characteristic sizes, and the determination part 840 may determine defectiveness/non-defectiveness of the workpiece 2 by using a result of the inspection by the flaw inspection part 831. Executing the flaw inspection on the plurality of inspection images eliminates the need for previously selecting one inspection image, which will be convenient for the user. The OCR part 832 may perform character recognition processing on a plurality of inspection images generated by using respectively different characteristic sizes, and the determination part 840 may determine defectiveness/non-defectiveness of the workpiece 2 by using a result of the character recognition by the OCR part 832. Performing the character recognition processing on the plurality of inspection images eliminates the need for previously selecting one inspection image, which will be convenient for the user.

Originally, a height image showing a height of the workpiece 2 can be generated by the photometric stereo method. However, measuring the height of the surface of the workpiece 2 requires a considerably strict setting for a positional relation between the camera 4 and the illumination apparatus 3. Meanwhile, out of images obtained by the photometric stereo method, shape information or texture (design) information can be used without acquiring height information. For example, when the flaw inspection or the OCR is to be performed, a strict setting for the camera 4 and the illumination apparatus 3 is not required. As thus described, when the inspection tool does not require accurate height data, it is possible to alleviate the arrangement conditions for the camera 4 and the illumination apparatus 3. Note that the number of illumination directions may be three or more.

The photometric processing part 811 may calculate a reflectance of the surface of the workpiece 2 along with a normal vector of the surface of the workpiece 2 from the plurality of luminance images acquired by the camera 4, to generate a reflectance image made up of pixel values based on the reflectance, and the determination part 840 may determine defectiveness/non-defectiveness of the workpiece 2 by using the reflectance image. This is because there also exists an inspection tool in which a reflectance image is suitably used for the inspection. The photometric processing part 811 may generate an inclination image made up of pixel values based on a normal vector of the surface of the workpiece 2 from the plurality of luminance images acquired by the camera 4, and the determination part 840 may determine defectiveness/non-defectiveness of the workpiece 2 by using the inclination image. This is because there also exists an inspection tool in which an inclination image is suitably used for the inspection. The determination part 840 may determine defectiveness/non-defectiveness of the workpiece 2 by using a luminance image. This is because there also exists an inspection tool in which a luminance image before being processed into an inclination image or a reflectance image is suitably used for the inspection. The determination part 840 may determine defectiveness/non-defectiveness of the workpiece 2 by using at least one luminance image out of a plurality of luminance images with respectively different illumination directions. Since there exists a flaw or the like that becomes clear by differences in the illumination direction, a luminance image obtained by illuminating the workpiece 2 from a certain direction is suitable for detecting such a flaw.

The determination part 840 may simultaneously light all the light sources of the illumination apparatus 3 and determine defectiveness/non-defectiveness of the workpiece 2 by using a luminance image acquired by the camera 4. That is, by using a so-called all-directional illumination image, whether the workpiece 2 is defective or non-defective may be determined. For example, the all-directional illumination image may be suitable for calculation of an area of a certain portion of the workpiece 2 or measurement of a length of a terminal.

The determination part 840 may synthesize a plurality of luminance images with respectively different illumination directions and determine defectiveness/non-defectiveness of the workpiece 2 by using the generated synthesized luminance image. The synthesized luminance image is an image similar to the all-directional illumination image. Therefore, by use of the synthesized luminance image in place of the all-directional illumination image, it is possible to execute the inspection without acquiring the all-directional illumination image. In the case where an all-directional illumination image is required, it is necessary to acquire four luminance images with respectively different illumination directions and one all-directional illumination image obtained by simultaneous illumination from four directions. That is, five times of illumination and five times of imaging are required. On the other hand, when the synthesized luminance image is used, four times of illumination and four times of imaging may be performed. In such a manner, adopting the synthesized luminance image can reduce a processing load of the processor 810 when a plurality of inspection images are required to be processed in a short period of time. Further, as the number of acquired images is increased, it becomes necessary to lower a conveying speed of the line 1. However, in the present embodiment, since the number of acquired images can be reduced, the conveying speed of the line 1 can be increased.

The storage device 820 may store and hold an inspection image. The determination part 840 or the image processing part 830 may read the inspection image from the storage device 820 and execute the inspection, to determine defectiveness/non-defectiveness of the workpiece 2 based on the inspection result. Note that the storage device 820 may be any of the internal memory, the portable type storage medium, and the network storage. For example, when an inspection image is stored into the portable type storage medium or the network storage, it is possible to perform inspection processing in an apparatus different from the apparatus that has generated the inspection image.

The storage device 820 may store a plurality of inspection images generated by applying characteristic sizes with respectively different values. In addition to the inspection image, the storage device 820 may store at least one of an inclination image and a reflectance image. The image selection part 816 may select one inspection image out of a plurality of inspection images. Further, the inspection tool setting part 817 may set an inspection tool for the inspection image selected by the image selection part 816. Among the plurality of inspection images generated by applying the characteristic sizes with respectively different values, an inspection image not required for the inspection may exist. Hence, the user may set an inspection image in accordance with an inspection tool.

As described using FIG. 15 and the like, the image processing part 830 may execute a pattern search by using a reference image acquired from a non-defective product, to set an inspection region. The determination part 840 may determine defectiveness/non-defectiveness of the workpiece 2 by using a result of the inspection executed in the inspection region. The inspection region is, for example, a character recognition region.

As described using FIG. 11 and FIGS. 21 to 26, the image selection part 816 may select an image, which is to be saved or outputted, out of a plurality of luminance images acquired by the camera 4 and an inspection image. Further, the image selection part 816 may select an image, which is to be saved or outputted, out of a plurality of luminance images, an inspection image, a luminance image acquired by lighting all of a plurality of light sources provided in the illumination apparatus 3, and a synthesized luminance image obtained by synthesizing the plurality of luminance images. Moreover, the image selection part 816 may select an image, which is to be saved or outputted, out of a plurality of inspection images with respectively different characteristic sizes. Furthermore, the image selection part 816 may select an image, which is to be saved or outputted, out of a plurality of luminance images, an inspection image, and a reflectance image whose pixel value is a reflectance of the surface of the workpiece 2. As thus described, allowing an image related to the inspection to be selected as appropriate will facilitate saving or outputting of a desired image.

The condition setting part 819 for setting a condition for saving or outputting an image may further be provided. For example, as described using FIGS. 22 and 26, the condition setting part 819 may, for example, set one of the mode for constantly saving or outputting an image, and the mode for saving or outputting an image when the determination part 840 determines that the workpiece 2 is not a non-defective product. As described using FIGS. 21 to 26, the processor 810 may judge whether or not the condition for saving or outputting an image is satisfied before or after the determination part 840 completes the determination. For example, whether or not an image is saved may be judged at the time point when the inspection is completed in the inspection flow, or whether or not an image is saved may be judged in any step of the inspection flow. In particular, in the latter case, it is also possible to save an intermediate image generated in the middle of the inspection flow. Such an intermediate image will be useful at the time of searching for a cause of failure in the inspection and adjusting a control parameter.

As described above, the photometric processing part 811 obtains a normal vector of the surface of the inspection target based on a plurality of luminance images acquired by the camera 4, to generate an inspection image made up of a plurality of pixel values in accordance with the normal vector. Further, the display control part 851 and the display part 7 switch and display at least one of the plurality of luminance images and the inspection image, or simultaneously display at least one of the plurality of luminance images and the inspection image. Moreover, the inspection tool setting part 817 functions as an adjustment section for adjusting at least one of a control parameter of the camera 4 and a control parameter of the illumination apparatus 3. Furthermore, when the control parameter is adjusted, the display control part 851 functions as an updating section for updating an image being displayed on the display part 7 to an image where the control parameter after the change has been reflected. As thus described, the luminance image and the inspection image used for inspection are switched and displayed, or these are simultaneously displayed, thereby allowing the user to instinctively see a result of adjustment of a parameter. This facilitates setting of a parameter at the time of generating an inspection image from an image acquired by using a photometric stereo principle.

As described concerning the shutter speed setting part 2703, when a shutter speed (exposure time) of the camera 4 is changed by the inspection tool setting part 817, the camera 4 captures an image of the workpiece 2 based on the exposure time, to acquire a plurality of luminance images. On the display part 7, the display control part 851 may switch and display, or simultaneously display, at least one luminance image out of a plurality of luminance images acquired after the change in exposure time and an inspection image regenerated based on this luminance image. When the shutter speed is changed, brightness of the luminance image changes, and a normal vector and a reflectance are also influenced by the change. That is, this change also has influences on an inclination image, a reflectance image and an inspection image (surface shape image, texture image) derivatively generated from these. Therefore, by adjusting the exposure time while checking the luminance image and the inspection image, it is possible to appropriately adjust the exposure time. In particular, since a change in exposure time is easier to check in the luminance image than in the inspection image, it is advantageous that the luminance image can be checked along with the inspection image.

As described concerning the light amount setting part 2706, when an illumination light amount is changed by the inspection tool setting part 817, an illumination light amount of each of a plurality of light sources provided in the illumination apparatus 3 is changed. That is, light amounts of illumination light from a plurality of directions are changed in conjunction with one another. Normally, each of light amounts of illumination light from a plurality of directions is the same. The light amount of illumination light also causes a change in image as does the shutter speed. Therefore, by adjusting the illumination light amount while checking the luminance image and the inspection image, it is possible to appropriately adjust the illumination light amount.

At the time of displaying a luminance image, the display control part 851 may emphasize pixels (saturated pixels) whose pixel values are saturated out of pixels constituting the luminance image. Further, as described concerning the notification part 2711, the display control part 851 may display information indicating a ratio of saturated pixel to pixels whose pixel values are not saturated (non-saturated pixels). Moreover, at the time of displaying a synthesized luminance image obtained by synthesizing a plurality of luminance images, the display control part 851 may emphasize saturated pixels out of pixels constituting the synthesized luminance image, or display information indicating a ratio of saturated pixels to non-saturated pixels. Saturated pixels such as overexposure and underexposure cause an error in calculation of a normal vector or a reflectance. Therefore, emphasis of saturated pixels facilitates adjusting a control parameter so as to sufficiently reduce the saturated pixels. At the time of displaying an inspection image, the display control part 851 may emphasize pixels whose coordinates match with those of pixels whose pixel values are saturated in a corresponding luminance image out of pixels of the inspection image, or display information indicating a ratio of saturated pixels to non-saturated pixels. As described above, in the inspection image such as the inclination image, pixels whose luminance is saturated cannot be discriminated. Therefore, by obtaining coordinates of saturated pixels in the luminance image and emphasizing pixels of the coordinates in the inspection image, the user can check presence or absence of saturated pixels just by checking the inspection image.

As described concerning the number-of-lighting-times setting part 2708, the inspection tool setting part 817 may adjust the number of lighting times of the illumination apparatus 3. Since the number of lighting times matches with the number of imaging times, when the number of lighting times increases, the number of illumination directions also increases. That is, the number of luminance images increases, and the accuracy in computing the inspection image also improves. Therefore, by checking the luminance image and the inspection image while adjusting the number of lighting times, it is possible to check to what extent the accuracy in computing the inspection image improves. When the number of lighting times is increased, an computing amount increases accordingly, and hence it is also be useful for finding a point of compromise between the number of lighting times and the accuracy in computing the inspection image.

As described concerning the lighting position adjusting part 2710, the inspection tool setting part 817 may change a light source to be lighted out of a plurality of light sources provided in the illumination apparatus 3. When the illumination apparatus 3 is erroneously installed, an illumination direction of the illumination apparatus 3 may be displaced from an illumination direction assumed in the photometric processing part 811. In FIG. 27, the arrow 2712 indicates the illumination direction assumed in the photometric processing part, and in this embodiment, the illumination direction of the illumination apparatus 3 matches with the illumination direction assumed in the photometric processing part. The user can readily discriminate that the illumination direction of the illumination apparatus 3 and the illumination direction assumed in the photometric processing part do not match with each other by checking the luminance image. When the illumination direction of the illumination apparatus 3 and the illumination direction assumed in the photometric processing part do not match, the user can adjust a lighting position of the light source (light-emitting element) by the lighting position adjusting part 2710, to make the illumination direction of the illumination apparatus 3 match with the illumination direction assumed in the photometric processing part.

As described concerning the lighting position adjusting part 2710, at the time of the inspection tool setting part 817 changing the light source to be lighted, the display control part 851 of the UI managing part 814 may display a user interface for designating the light source to be lighted. The inspection tool setting part 817 may accept designation of the light source to be lighted in the user interface. For example, the UI managing part 814 may display a UI showing arrangement (circular arrangement, rectangular arrangement, and the like) of the light sources and accept, on that UI, designation of the illumination direction (light source group) corresponding to the current luminance image.

As described using FIGS. 28 and 31, when the display control part 851 is displaying the inspection image, the inspection tool setting part 817 may adjust a generation condition for the inspection image by the photometric stereo method. A representative condition out of the generation conditions is a characteristic size. Since the display control part 851 switches and displays, or simultaneously displays, a plurality of inspection images with respectively different generation conditions, the user can easily find an appropriate generation condition while checking an influence of the generation condition. As described using FIG. 29, the display control part 851 may display one inspection image selected out of the plurality of inspection images with respectively different generation conditions. The photometric processing part may regenerate one selected inspection image in accordance with the characteristic size adjusted by the inspection tool setting part 817, and the display control part 851 may display the regenerated inspection image on the display part 7. The generation conditions include a common setting item that is commonly set for a plurality of inspection images and individually setting items that are individually set for a plurality of inspection images. For example, exposure time, dark-part change control, halation removal, and the like are items that are commonly set for each luminance image. Meanwhile, a characteristic size, a guided filter, texture removal and the like are items that are individually set for each of the plurality of inspection images. Separating the individually setting item and the common setting item in such a manner allows adjustment to be efficiently performed.

The display control part 851 may switch and display, or simultaneously display, an inclination image made up of pixel values in accordance with a normal vector of the surface of the workpiece 2 and a reflectance image made up of pixel values in accordance with a reflectance of the surface of the workpiece 2. Since the different types of inspection images can be checked together with the luminance image as thus described, the user can judge whether or not a control parameter is suitable for the inspection image.

What is claimed is:

1. An inspection apparatus comprising:
   an illumination section for illuminating an inspection target by a photometric stereo method;
   an imaging section for capturing an image of the inspection target illuminated by the illumination section;
   an inspection image generating section for obtaining a normal vector of a surface of the inspection target based on a plurality of luminance images acquired by the imaging section, to generate an inspection image made up of a plurality of pixel values in accordance with the normal vector;
   a display section for switching and displaying at least one of the plurality of luminance images and the inspection image, or simultaneously displaying at least one of the plurality of luminance images and the inspection image;
   an adjustment section for adjusting at least one of a control parameter of the imaging section and a control parameter of the illumination section; and
   an updating section for updating an image being displayed on the display section to an image where the control parameter has been reflected when the control parameter is adjusted, wherein, when the display section displays the inspection image, the adjustment section adjusts a generation condition for the inspection image by the photometric stereo method, and the adjustment section adjusts a characteristic size out of the generation conditions.

2. The inspection apparatus according to claim 1, wherein, when the adjustment section changes exposure time of the imaging section, the imaging section captures an image of the inspection target based on the exposure time to acquire a plurality of luminance images, and
   the updating section switches and displays, or simultaneously displays, at least one of the plurality of luminance images acquired after the exposure time is changed and the inspection image on the display section.

3. The inspection apparatus according to claim 1, wherein, when an illumination light amount is changed by the adjustment section, an illumination light amount of each of a plurality of light sources provided in the illumination section is changed.

4. The inspection apparatus according to claim 1, wherein, at the time of displaying a luminance image, the display section emphasizes pixels whose pixel values are saturated out of pixels constituting the luminance image, or displays information indicating a ratio of pixels whose pixel values are saturated to pixels whose pixel values are not saturated.

5. The inspection apparatus according to claim 1, wherein, at the time of displaying a synthesized luminance image obtained by synthesizing the plurality of luminance images, the display section emphasizes pixels whose pixel values are saturated out of pixels constituting the synthesized luminance image, or displays information indicating a ratio of pixels whose pixel values are saturated to pixels whose pixel values are not saturated.

6. The inspection apparatus according to claim 1, wherein, at the time of displaying the inspection image, the display section emphasizes pixels whose coordinates match with those of pixels whose pixel values are saturated in the luminance image out of pixels of the inspection image, or displays information indicating a ratio of pixels whose pixel values are saturated to pixels whose pixel values are not saturated.

7. The inspection apparatus according to claim 1, wherein the adjustment section adjusts the number of lighting times of the illumination section.

8. The inspection apparatus according to claim 1, wherein the adjustment section changes a light source to be lighted out of a plurality of light sources provided in the illumination section.

9. The inspection apparatus according to claim 8, wherein
   the display section displays a user interface for designating the light source to be lighted when the adjustment section changes the light source to be lighted, and
   the adjustment section accepts designation of the light source to be lighted in the user interface.

10. The inspection apparatus according to claim 1, wherein the display section switches and displays, or simultaneously displays, a plurality of inspection images whose generation conditions are respectively different.

11. The inspection apparatus according to claim 1, wherein
    the display section displays one inspection image selected out of a plurality of inspection images whose generation conditions are respectively different,
    the inspection image generating section regenerates the one selected inspection image in accordance with the characteristic size adjusted by the adjustment section, and
    the updating section displays the regenerated inspection image on the display section.

12. The inspection apparatus according to claim 1, wherein the generation conditions include a common setting item that is commonly set for a plurality of inspection images and individual setting items that are individually set for the plurality of inspection images.

13. The inspection apparatus according to claim 1, further comprising
    an image selection section for selecting an image, which is to be saved or outputted, out of a plurality of luminance images acquired by the imaging section and the inspection image.

14. The inspection apparatus according to claim 13, wherein the image selection section selects an image, which is to be saved or outputted, out of the plurality of luminance images, the inspection image, a luminance image acquired by lighting all of the plurality of light sources provided in the illumination sections, and a synthesized luminance image obtained by synthesizing the plurality of luminance images.

15. The inspection apparatus according to claim 13, wherein the image selection section selects an image, which is to be saved or outputted, out of the plurality of inspection images with respectively different characteristic sizes.

16. The inspection apparatus according to claim 13, wherein the image selection section selects an image, which is to be saved or outputted, out of the plurality of luminance images, the inspection image, and a reflectance image whose pixel value is a reflectance of the surface of the inspection target.

17. A control method for an inspection apparatus which includes
    an illumination section for illuminating an inspection target by a photometric stereo method;
    an imaging section for capturing an image of the inspection target illuminated by the illumination section;

an inspection image generating section for obtaining a normal vector of the surface of the inspection target based on a plurality of luminance images acquired by the imaging section, to generate an inspection image made up of a plurality of pixel values in accordance with the normal vector; and a display section for switching and displaying at least one of the plurality of luminance images and the inspection image, or simultaneously displaying at least one of the plurality of luminance images and the inspection image, the method comprising:

an adjustment step of adjusting at least one of a control parameter of the imaging section and a control parameter of the illumination section, wherein, when the display section displays the inspection image, the adjustment step adjusts a generation condition for the inspection image by the photometric stereo method, and the adjustment step adjusts a characteristic size out of the generation conditions; and an updating step of updating an image being displayed on the display section to an image where the control parameter has been reflected when the control parameter is adjusted.

18. A computer storing a program which causes the computer to function as:

an illumination section for illuminating an inspection target by a photometric stereo method;

an imaging section for capturing an image of the inspection target illuminated by the illumination section;

an inspection image generating section for obtaining a normal vector of the surface of the inspection target based on a plurality of luminance images acquired by the imaging section, to generate an inspection image made up of a plurality of pixel values in accordance with the normal vector;

a display section for switching and displaying at least one of the plurality of luminance images and the inspection image, or simultaneously displaying at least one of the plurality of luminance images and the inspection image;

an adjustment section for adjusting at least one of a control parameter of the imaging section and a control parameter of the illumination section, wherein, when the display section displays the inspection image, the adjustment section adjusts a generation condition for the inspection image by the photometric stereo method, and the adjustment section adjusts a characteristic size out of the generation conditions; and an updating section for updating an image being displayed on the display section to an image where the control parameter has been reflected when the control parameter is adjusted.

* * * * *